(12) United States Patent
Ding et al.

(10) Patent No.: US 10,258,573 B2
(45) Date of Patent: Apr. 16, 2019

(54) MICRONIZED INSULIN AND MICRONIZED INSULIN ANALOGUES PREPARED UNDER ACIDIC CONDITIONS, AND METHODS OF MANUFACTURING THE SAME UNDER ACIDIC CONDITIONS

(71) Applicant: AMPHASTAR PHARMACEUTICALS INC., Rancho Cucamonga, CA (US)

(72) Inventors: Jeffrey Ding, Rancho Cucamonga, CA (US); Aili Bo, Rancho Cucamonga, CA (US); Mary Ziping Luo, Rancho Cucamonga, CA (US); Jack Yongfeng Zhang, Rancho Cucamonga, CA (US)

(73) Assignee: Amphastar Pharmaceuticals, Inc., Rancho Cucamonga, CA (US)

(*) Notice: Subject to any disclaimer, the term of this patent is extended or adjusted under 35 U.S.C. 154(b) by 0 days.

(21) Appl. No.: 14/794,766

(22) Filed: Jul. 8, 2015

(65) Prior Publication Data
US 2016/0008287 A1    Jan. 14, 2016

Related U.S. Application Data

(60) Provisional application No. 62/022,026, filed on Jul. 8, 2014.

(51) Int. Cl.
| | | |
|---|---|---|
| *A61K 9/14* | (2006.01) | |
| *A61K 9/16* | (2006.01) | |
| *A61K 9/00* | (2006.01) | |
| *A61K 38/28* | (2006.01) | |

(52) U.S. Cl.
CPC ............ *A61K 9/1688* (2013.01); *A61K 9/008* (2013.01); *A61K 9/0075* (2013.01); *A61K 9/14* (2013.01); *A61K 9/1617* (2013.01); *A61K 38/28* (2013.01)

(58) Field of Classification Search
CPC .... A61K 9/1688; A61K 9/0075; A61K 9/008; A61K 9/14; A61K 9/1617; A61K 38/28
See application file for complete search history.

(56) References Cited

U.S. PATENT DOCUMENTS

| | | | |
|---|---|---|---|
| 5,952,297 A * | 9/1999 | De Felippis | C07K 14/62 514/5.9 |
| 5,985,309 A | 11/1999 | Edwards et al. | |
| 6,051,256 A | 4/2000 | Platz et al. | |
| 6,090,925 A | 7/2000 | Woiszwillo et al. | |
| 6,221,398 B1 * | 4/2001 | Jakupovic | A61K 9/0075 424/489 |
| 6,310,038 B1 | 10/2001 | Havelund | |
| 6,444,226 B1 | 9/2002 | Steiner et al. | |
| 6,582,728 B1 | 6/2003 | Platz et al. | |
| 6,652,885 B2 | 11/2003 | Steiner et al. | |
| 7,087,246 B2 | 8/2006 | Kim et al. | |
| 7,374,782 B2 | 5/2008 | Brown | |
| 7,521,069 B2 | 4/2009 | Patton et al. | |
| 7,625,865 B2 | 12/2009 | Colombo et al. | |
| 7,648,960 B2 | 1/2010 | Steiner et al. | |
| 7,803,763 B2 * | 9/2010 | Thurow | C07K 14/62 514/5.9 |
| 7,943,178 B2 | 5/2011 | Steiner et al. | |
| 8,075,919 B2 | 12/2011 | Brown et al. | |
| 8,389,470 B2 | 3/2013 | Steiner et al. | |
| 2006/0292224 A1 * | 12/2006 | Moore | A61K 9/145 424/489 |
| 2008/0026068 A1 * | 1/2008 | Brown | A61K 9/0075 424/489 |
| 2016/0008287 A1 | 1/2016 | Ding et al. | |

FOREIGN PATENT DOCUMENTS

| | | | |
|---|---|---|---|
| EP | 0709395 A2 | 5/1996 | |
| EP | 0 735 048 A1 | 10/1996 | |
| EP | 0735048 A1 | 10/1996 | |
| EP | 2 036 572 A1 * | 3/2009 | |
| EP | 3166595 A1 | 5/2017 | |
| JP | 2007531701 A | 11/2007 | |
| WO | WO 98/42749 | 10/1998 | |
| WO | WO 98/42749 A1 | 10/1998 | |
| WO | WO 01/00674 A1 | 1/2001 | |
| WO | WO 2005/032511 A2 | 4/2005 | |
| WO | WO 2005/035088 A2 | 4/2005 | |
| WO | WO 2005/932511 * | 4/2005 | .............. A61K 9/00 |
| WO | WO 2013115965 A1 | 8/2013 | |
| WO | WO 2016/007682 A1 | 1/2016 | |
| WO | WO 2016/007682 A1 | 1/2016 | |

OTHER PUBLICATIONS

Biological Buffers, AppliChem, 2008, 20 pages.*
Sigma, Product Information for Insulin from bovine pancreas, Cat. Nos. including I5500, 2 pages, copyright 2014.*
Vandana et al., An overview on in situ micronization technique—An emerging novel concept in advanced drug delivery, Saudi Pharm. Jl. (2014) 22, 283-289.*
Vandana et al., An overview on in situ micronization technique—An emerging novel concept in advanced drug delivery, Saudi Pharm. Jl. (2014) 22, 283-289.*
Sigma Product Information, Product Nos. I0259 and I2767, 2 pages, Jan. 21, 1999.*
H. M. Lando, The New "Designer" Insulins, Clinical Diabetes, vol. 18, No. 4, Fall 2000, pp. 1-12.*
Bailey et al., Pure Insulin Nanoparticle Agglomerates for Pulmonary Delivery, Langmuir, 2008 24(23):13614-13620.*
Ask the TA—Chemistry Help, 2008, 4 pages, sourced online.*
Somogyi et al, Jl Biol. Chem. 1924, 60: 31-58.*
International Search Report dated Sep. 8, 2015 of the corresponding International Patent Application No. PCT/US2015/039625, noting listed references in this IDS (11 pages).

(Continued)

*Primary Examiner* — Karlheinz R. Skowronek
*Assistant Examiner* — Joseph Fischer
(74) *Attorney, Agent, or Firm* — Lewis Roca Rothgerber Christie LLP

(57) ABSTRACT

A method of preparing an inhalable insulin suitable for pulmonary delivery includes: dissolving an insulin raw material in an acidic solution to form a dissolved insulin solution; titrating the dissolved insulin solution with a buffer solution to form a suspension comprising micronized insulin particles; and stabilizing the micronized insulin particles.

20 Claims, 17 Drawing Sheets

(56) References Cited

OTHER PUBLICATIONS

Figure 1:
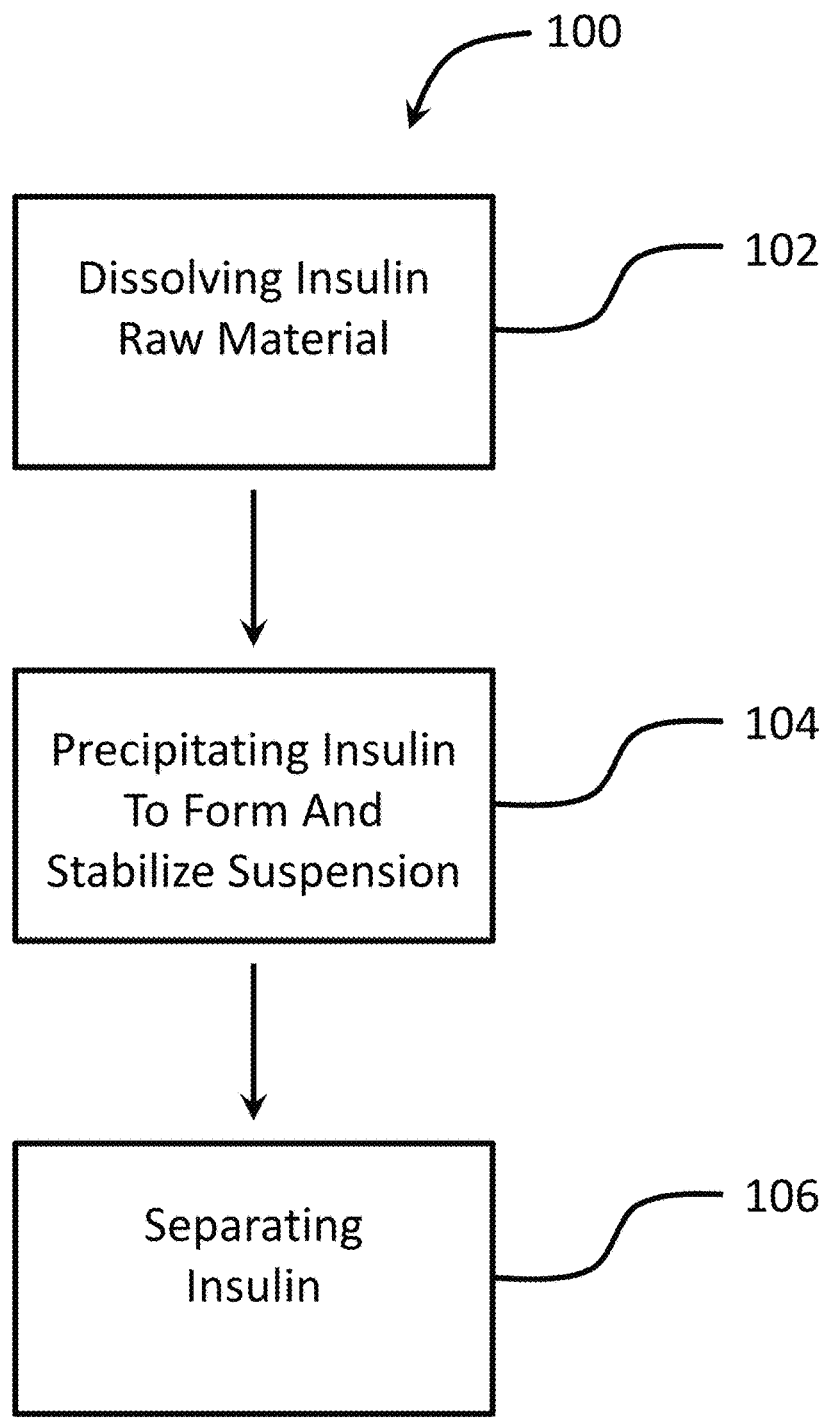

Black, C., et al., "The clinical effectiveness and cost-effectiveness of inhaled insulin in diabetes mellitus: a systematic review and economic evaluation," Health Technology Assessment, vol. 11, No. 33, Sep. 2007, pp. 1-126.
Butterfield, Timothy A., et al., "The Dual Roles of Neutrophils and Macrophages in Inflammation: A Critical Balance Between Tissue Damage and Repair," Journal of Athletic Training, vol. 41, No. 4, 2006, pp. 457-465.
Chordiya, Gangurde H.H., et al., "Approaches and Devices Used in Pulmonary Drug Delivery System: a Review," Asian Journal of Pharmaceutical Research & Health Care, vol. 4, No. 1, 2012, pp. 11-27.
Chow, Albert H. L., et al., "Particle Engineering for Pulmonary Drug Delivery," Pharmaceutical Research, vol. 24, No. 3, Mar. 2007, pp. 411-437.
Ehmer, Alex, "Micronization of Proteins by Jet Milling," Dissertation, Universität Regensburg, 2009, Chapter 1, p. 8.
"FDA Approves First Ever Inhaled Insulin Combination Product for Treatment of Diabetes," News & Events, Jan. 27, 2006 (3 pages).
Heyder, Joachim, "Deposition of Inhaled Particles in the Human Respiratory Tract and Consequences for Regional Targeting in Respiratory Drug Delivery," Proceedings of the American Thoracic Society, vol. 1, 2004, pp. 315-320.
Pikal, M. J., et al., "Formulation and Stability of Freeze-Dried Proteins: Effects of Moisture and Oxygen on the Stability of Freeze-Dried Formulations of Human Growth Hormone," International Symposium on Biological Product Freeze-Drying and Formulation, vol. 74, 1990, pp. 21-38.

Ragab, Doaa M., et al., "Particle Engineering Strategies via Crystallization for Pulmonary Drug Delivery," Organic Process Research & Development, vol. 13, No. 6, 2009, pp. 1215-1223.
Skyler, Jay, "Pulmonary insulin: current status," Diabetes Voice, vol. 51, Issue 1, Mar. 2006, pp. 23-25.
Whittingham, Jean L., et al., "Insulin at pH 2: Structural Analysis of the Conditions Promoting Insulin Fibre Formation," J. Mol. Biol., vol. 318, No. 2, 2002, pp. 479-490.
PCT International Search Report and Written Opinion dated Jun. 22, 2016 for International Application No. PCT/US2016/012715, 13 pages.
Gupte, Suraj, "Noninvasive Delivery of Insulin Pulmonary Delivery," p. 325 of *Recent Advances in Pediatrics—17: Hot Topics*, First Edition 2007 ISBN 81-8448-103-9, 3 pages.
Office Action issued in Canadian Patent Application No. 2,954,287, dated Feb. 13, 2018, 4 pages.
Hallas-Moller, K., et al., Crystalline and Amorphous Insulin-Zinc Compounds with Prolonged Action, Science, vol. 116, Oct. 10, 1952, 5 pages.
Jiang, C., et al., Unfolding and breakdown of insulin in the presence of endogenous thiols, FEBS Letters, 579, 2005, pp. 3927-3931.
Japan Office action issued in JP2017-500986 dated Oct. 31, 2017, 9 pages.
Russian Office action issued in Application No. 2017103751, dated Apr. 5, 2018, 18 pages.
U.S. Office action issued in U.S. Appl. No. 15/280,508, dated Oct. 24, 2017, 13 pages.
U.S. Office action issued in U.S. Appl. No. 14/990787, dated Apr. 24, 2018, 11 pages.
Office action issued in Japanese Patent Application No. 2017-500986, Oct. 2, 2018, 12 pages.
Koichi Katoh, "Acidity in water-alcohol mixtures," Bunseki Kagaku, vol. 15, Issue 8, 1966, pp. 811-816.

* cited by examiner

MICRONIZED INSULIN AND MICRONIZED INSULIN ANALOGUES PREPARED UNDER ACIDIC CONDITIONS, AND METHODS OF MANUFACTURING THE SAME UNDER ACIDIC CONDITIONS

CROSS-REFERENCE TO RELATED APPLICATION(S)

The present application claims priority to and the benefit of U.S. Provisional Application No. 62/022,026, filed in the United States Patent and Trademark Office on Jul. 8, 2014, the entire content of which is incorporated herein by reference.

FIELD

Embodiments of the invention relate in general to pulmonary delivery of human insulin and/or a human insulin analogue, and a process for micronizing human insulin and/or a human insulin analogue for pulmonary delivery. Aspects of embodiments of the disclosure also relate in general to compositions including a micronized human insulin and/or a micronized human insulin analogue having improved particle characteristics.

BACKGROUND

Growing attention has been given to the potential of a pulmonary absorption route for non-invasive administration and systemic delivery of therapeutic agents (mainly peptides and proteins) because the lungs are capable of providing a large absorptive surface area (up to 100 m$^2$) and have absorptive mucosal membranes that are very or extremely thin (e.g., have a thickness of about 0.1 µm-0.2 µm) and have good blood supply. A very thin alveolar-capillary and a bronchial-capillary barrier on a surface of the lungs allows for rapid uptake of human insulin particles into a subject's bloodstream, at a rate similar to that achieved with the rapid-acting human insulin analogue, which is an altered form of human insulin that is different from human insulin that occurs in nature, but still functions in the human body in a manner similar to human insulin, but with better performance in terms of glycemic control.

Insulin formulations may be administered by subcutaneous or intravenous injection. Inhaled insulin appears to be as effective as injected short-acting insulin. Pulmonary delivery technology was developed so that inhaled insulin can effectively reach the lung capillaries where it is absorbed.

Human lung airways contain bronchial tubes, which are impermeable to insulin, as well as alveoli. Inhaled insulin can be absorbed through the alveoli and enter into the circulation system. Inhaled asthma medications deposit before reaching the alveoli. Devices can deliver human insulin particles via slow and even breaths into the alveoli, and the human insulin can be released into the circulation system.

Inhaled human insulin may be used for pre-meal insulin delivery in people with type I and/or II diabetes. Its use may also facilitate the early introduction of insulin therapy to people who are averse to insulin injections due to reactions, such as inflammation, bruising, anxiety, and the like.

SUMMARY

According to an embodiment of the present disclosure, a method of preparing an inhalable human insulin suitable for pulmonary delivery includes: dissolving an insulin raw material in an acidic solution to form a dissolved human insulin solution; titrating the dissolved insulin solution with a buffer solution to form a suspension comprising micronized insulin particles; and stabilizing the micronized insulin particles.

The acidic solution may include water, an organic solvent, or a mixture thereof.

The acidic solution may include the organic solvent in an amount of 10 to 90 vol %, based on the total volume of the acidic solution.

The acidic solution may include the organic solvent in an amount of greater than 0 to 90 vol % of the total volume of the acidic solution.

The organic solvent may include an alcohol.

The alcohol may include methanol, ethanol, or a mixture thereof.

The buffer solution may have a pH of 3 to 10.

The stabilizing of the micronized insulin particles may include adding a stabilizing agent to the suspension.

The stabilizing agent may have a neutral pH and may be miscible with water.

The stabilizing agent may include an alcohol, a ketone, or a mixture thereof.

The stabilizing may increase the yield of the micronized insulin particles.

The micronized insulin particles may be prepared at a pH of 3 to 9.

The micronized insulin particles may be prepared at a pH of 4.5 to 7.5.

The micronized insulin particles may include substantially spherical particles having a volume mean diameter of about 1.2 to 2 µm.

The micronized insulin particles may include up to 99 vol % of particles having a particle size of less than 5 µm, based on the total volume of the micronized insulin particles.

The acidic solution may have a pH range of 1.0 to 3.0. For example, the acidic solution may have a pH in a range of 1.8 to 2.2.

The acidic solution may have a pH of about 2 and may include water and 10 vol % to 90 vol % of an organic solvent including methanol, ethanol, or a mixture thereof, based on the total volume of the acidic solution.

The micronized insulin particles may be substantially spherical in shape and may have a particle size of less than 5 µm.

The micronized insulin particles may include an insulin including human insulin, an animal insulin, an insulin analogue, or a mixture thereof.

The insulin analogue may include insulin aspart, insulin glargine, or a mixture thereof.

The dissolving, the titrating, and/or the stabilizing procedures may be performed at room temperature.

The insulin raw material may include a crystalline insulin including crystalline human insulin, a crystalline animal insulin, a crystalline insulin analogue, or a mixture thereof.

The crystalline insulin analogue may include crystalline insulin aspart, crystalline insulin glargine, or a mixture thereof.

According to an embodiment of the present disclosure, micronized insulin particles include substantially spherical particles comprising an insulin selected from the group consisting of human insulin, an animal insulin, an insulin analogue, and a mixture thereof.

The substantially spherical particles may have a volume mean diameter of about 1.2 to 2 µm.

Up to 99 vol % of the substantially spherical particles may have a particle size of less than 5 μm, based on the total volume of the micronized insulin particles.

The insulin analogue may include insulin aspart, insulin glargine, or a mixture thereof.

The foregoing description of embodiments of the present disclosure is not meant to be an exhaustive summary, inasmuch as additional pertinent aspects of the present disclosure will be readily apparent to those skilled in the art from the following detailed description, taken independently or in conjunction with the accompanying drawings and tables, in which one or more embodiments of the invention are described and shown.

BRIEF DESCRIPTION OF THE DRAWINGS

The accompanying drawings, together with the specification, illustrate embodiments of the present disclosure, and, together with the description, serve to explain the principles of the present disclosure.

FIG. 1 is a flow chart illustrating an embodiment of a process for micronizing insulin and/or an insulin analogue.

FIG. 2 is a Scanning Electron Microscopy (SEM) Image of micronized human insulin particles prepared according to an embodiment of the present disclosure.

FIG. 3 is a graph illustrating a particle size distribution of micronized human insulin particles prepared according to the embodiment of FIG. 2.

FIG. 4 is a chart showing an impurity profile of human insulin before and after micronizing according to an embodiment of the present disclosure.

FIG. 5 is a high-performance liquid chromatography (HPLC) chromatograph of dissolved, micronized insulin particles prepared according to an embodiment of the present disclosure.

FIGS. 6 and 7 are charts showing data from an Andersen Cascade Impactor study of human insulin particles delivered from a filled canister as prepared according to an embodiment of the present disclosure.

FIG. 8 is a Scanning Electron Microscopy (SEM) image of micronized insulin glargine particles prepared according to an embodiment of the present disclosure.

FIG. 9 is an HPLC chromatograph of dissolved, micronized insulin glargine particles prepared according to the embodiment of FIG. 8.

FIGS. 10 and 11 are charts showing the results of an Andersen Cascade Impactor study of insulin glargine particles delivered from a filled canister as prepared according to the embodiment of the present disclosure.

FIG. 12 is a Scanning Electron Microscopy (SEM) image of micronized insulin aspart particles prepared according to an embodiment of the present disclosure.

FIG. 13 is an HPLC chromatograph of dissolved micronized insulin aspart particles prepared according to the embodiment of FIG. 12.

FIGS. 14 and 15 are charts showing results of an Andersen Cascade Impactor study of insulin aspart particles delivered from a filled canister as prepared according to the embodiment of the present disclosure.

FIG. 16 is an Atom Force Microscopy (AFM) image of human insulin particles prepared according to a jet milling method.

FIG. 17 is an Atom Force Microscopy (AFM) image of micronized insulin particles that were prepared as described with respect to Example 2.

DETAILED DESCRIPTION

The following detailed description is provided only for purposes of illustration of certain specific embodiments of the present disclosure and not for purposes of limiting the scope of the present invention. Alternate embodiments will be readily apparent to those skilled in the art and are intended to be included within the scope of the present invention. Also, in the context of the present application, the term "insulin" is used in a broad sense and encompasses any form of insulin or insulin analogue that can be used to treat a human or animal. For example, as used herein, the term "insulin" encompasses natural or synthetic human insulin, natural or synthetic animal insulin, and insulin analogues (e.g., insulin aspart, insulin glargine, and the like).

An embodiment of a micronization process for preparing inhalable insulin particles for pulmonary delivery includes: dissolving an insulin raw material (e.g., a crystalline insulin and/or a crystalline insulin analogue) in an acidic environment (e.g., dissolving in an acidic solution to facilitate dissolution of the insulin raw material) to form a dissolved insulin solution; titrating the dissolved insulin solution with a buffer solution to form a suspension including micronized insulin particles; and adding a stabilizing agent (e.g., an organic solvent and/or a co-solvent) to stabilize the micronized insulin particles (e.g., to increase the yield of the micronized insulin particles before purification and drying). Embodiments of the process are conducted at room temperature and avoid or reduce the introduction of heat and/or mechanical forces such as those introduced by lyophilization, microsphere, and jet milling processes. Some embodiments of the process are performed without addition of a polymer (e.g., an excipient polymer) to the acidic environment, including the dissolved insulin solution and/or the suspension.

Embodiments of the present invention provide a process for the production of inhalable insulin that is suitable for pulmonary delivery. Embodiments of the process utilize raw crystalline insulin, which may have a particle size in a millimeter range, to provide inhalable insulin particles having a particle size in a micrometer range as an active pharmaceutical ingredient (API) for pulmonary delivery having improved characteristics, including more spherical shape, as well as improved smoothness. As described herein, the particle size or particle diameter (e.g., volume mean diameter) may be measured by a laser diffraction method, unless otherwise specified.

Pulmonary delivery of a drug particle is affected by the characteristics of the drug particle including particle size, particle shape, surface roughness, solubility, flowability, and/or the like. Since inhalable insulin and/or insulin analogues are an active drug ingredient and not just a passive carrier, embodiments of the present disclosure maintain or substantially maintain biological activities while micronizing the insulin and insulin analogues.

A particle having a particle size (or an aerodynamic diameter) of <5 μm allows for the inhaled drug to be absorbed by the lungs. Particles having a suitable aerodynamic diameter or particle size have good flow properties and are more easily dispersed into the lower airways (bronchial and alveolar regions) in which the absorption into the bloodstream is improved or optimized via alveolar-capillary surfaces of the lungs. On the other hand, over-sized drug particles (e.g., particles having an aerodynamic diameter or particle size >5 μm) would be mostly captured in the upper airways such as the throat and trachea by inertial impaction. The over-sized particles are substantially not absorbed as they accumulate in the upper airways, which do not have the thin penetrable capillaries of the alveoli. The accumulated drug particles may trigger the pulmonary defense system, which may prompt macrophages increment. The stimulation or excessive stimulation of macrophages may lead to recruitment of other inflammatory cells and may eventually produce secondary tissue damage, regeneration and fibrosis.

Drug particle size may play a determinant role in pulmonary delivery. To fabricate particles having a particle diameter <5 µm, a number of single-step micronization methods may be used, such as spray drying and mechanical milling technologies, such that after the process, the starting raw insulin powder particles, which in general have a diameter of millimeter range, have a diameter in a micrometer range for pulmonary delivery.

However, those processes for micronizing insulin particle involve introduction of heat and/or excipient polymer during the insulin micronization process, which may cause aggregation and loss of activity of the insulin, and may hinder pharmaceutical manufacturing. In addition, although the excipient polymer helps to stabilize the formulation and increase the solubility during processing, the excipient polymer may introduce impurities that are difficult to remove.

A lyophilization process may be used to transform the insulin particle from the millimeter sized range (e.g., raw insulin) to a micrometer sized range. One reason for using lyophilization is that production of particles in the 1-5 µm range is at the limit of the size reduction capability of this method. Polymer(s) may also be introduced as an inactive substance or excipient in the formulation to improve stability and solubility.

The lyophilized micronizing process, however, may be potentially hazardous to macromolecules, such as insulin. For example, during the lyophilization process, heat is supplied to the molecule to sublime water, which may lead to a conformational change in the insulin and may even denature the insulin. It has been shown that heat and agitation promote fibril formation in insulin.

Moreover, the rate of cooling of the lyophilization process (polythermal process) is claimed to control the size and shape of the micro-particles, but the lyophilization may cause over-drying of the micro-particles of insulin formed by the insulin and the polymer and may result in decreased chemical or physical stability. Insulin is also more susceptible to be aggregated in a dried powder state.

It has also been found that micro-particles of insulin are formed by dissolving crystalline insulin at a pH near the isoelectric point of the insulin, when a polymer is used in the process of forming the insulin micro-particles. Various suitable types of polymers such as polyethylene glycol (PEG), polyvinylpyrrolidone (PVP), poly-lactic acid-co-glycolide acid (PLGA), as well as bioadhesive mechanisms, may be used in the process. When the polymer is added to the buffer solution, it may help to further increase the solubility of the crystalline insulin. However, the added polymer may not be efficiently and completely removed after the process. The residual polymer that is not removed may reduce drug efficacy, increase toxicity, and increase the level of impurities.

Other processes related to the production of microspheres that contain insulin introduce excipient polymers such as PVP, or PEG to help dissolve insulin in an acidic environment. Microspheres produced by such processes are exposed to relatively high temperatures that may be hazardous or damaging to insulin. At the end of such processes, an organic solvent (which has low solubility for insulin) for washing the polymer away may cause agglomeration of small insulin particles. Also, the foregoing organic solvents can denature insulin molecules contained in the microspheres and may also be toxic when administered to humans or animals.

Processes of fabrication of insulin micro-particles other than those of embodiments of the present disclosure utilize organic solvents, and need harsh sterilization condition. The organic solvents (other than those of the present disclosure) may affect drug purity and may be harmful in vivo if residual organic solvent remains in the microspheres. Additionally, porous structures caused by organic solvent may lead to inconsistency in the emitted dose. Sterilization by thermal, chemical, or radiation processes may cause degradation of the polymer and/or drug entrapped in the microspheres. Sterilizing solutions may also increase the amount of impurities present.

A controlled release preparation of insulin may contain microspheres obtained by microencapsulation (e.g., by way of a surfactant) of uniform microcrystals of insulin using biodegradable polymeric materials. Such compositions, however, may have a low insulin content, for example, an average insulin particle may contain less than 10% w/w, based on the total weight of the insulin particle.

Aspects of embodiments of the present disclosure are directed toward overcoming the above-mentioned difficulties. An embodiment of a method of manufacturing an inhalable insulin or insulin analogue may include the following three (3) actions:

(1) Dissolving an insulin raw material (e.g., crystalline insulin or insulin analogue) in an acidic environment to facilitate dissolution of the insulin raw material, thereby forming a dissolved insulin solution. The acidic environment may include an acidic solution. For example, the acidic environment may include an acidic solution including water, an organic solvent (e.g., an alcohol, such as methanol), or a mixture thereof.

The behavior of insulin in an acidic environment may be utilized to dissolve insulin. In some embodiments, the acidic environment has a pH of about 1.0 to 3.0, for example, 1.8 to 2.2, to provide good dissolution conditions.

(2) Titrating the dissolved insulin solution with a buffer solution until the status of a suspension is reached (e.g., until a suspension is obtained). The titrating of the dissolved insulin solution may be utilized to change the solubility of the dissolved insulin and to cause the dissolved insulin to precipitate as micronized insulin particles and form a suspension. For example, the pH value of the solution may be changed to affect the solubility of the insulin. Insulin includes both acidic and basic functional groups. Amino acids (e.g., the amino groups and carbonyl groups) that constitute insulin may have a positive charge, a negative charge, or may be neutral, and together provide insulin with its overall charge. At a pH below its isoelectric point (IEP), insulin carries a net positive charge, while above its IEP insulin carries a net negative charge. Thus, the dissolved insulin solution may be titrated to approach a pH close to the value of the IEP of insulin to reduce the solubility of the insulin and to solidify and precipitate the insulin out of the dissolved insulin solution as small or tiny particles having a particle size in the micrometer range. As insulin precipitates the dissolved insulin solution changes from a clear or substantially clear solution to a milky and whitish suspension (e.g., the suspension including micronized insulin particles).

(3) Stabilizing the micronized insulin particles by adding a stabilizing agent (e.g., an organic solvent and, optionally, a co-solvent) to increase the yield of the micronized insulin particles before purification and drying.

The stabilizing agent (e.g., the organic solvent and/or co-solvent) may be added to increase the yield of the micronized insulin particles. The stabilizing agent (e.g., the organic solvent and, optionally, the co-solvent) utilized may be varied according to the type of insulin and will be further described in the following section.

Aspects of embodiments of the present disclosure provide the following features: simpler and safer manufacturing and/or end product as compared to lyophilization, polymer, and microspherical methods; no excipient polymer (which may introduce additional impurities) is required; micronization process may be conducted at about room temperature; no or substantially no loss of molecular activity of the insulin; and less aggregation and/or degradation of the insulin due to no need of additional heat.

Embodiments of the novel process for micronizing insulin and insulin analogues at room temperature for pulmonary delivery according to the present disclosure include the following three major actions. First, dissolution of an insulin raw material having a particle size in a millimeter range; second, micronization (e.g., precipitation of insulin particles such that the solution including the insulin particles becomes a suspension including micronized insulin particles); third, stabilizing the micronized insulin particles; and fourth, separation of the insulin particles from the liquid solution. The separation of the insulin particles from the liquid solution may be followed by washing, drying and purification to complete an embodiment of the process of fabricating inhalable insulin or insulin analogue API.

In the first action, the insulin raw material may be dissolved in an acidic environment (e.g., an acidic solution) including water and an organic solvent that is polar, has a small molecular weight and is miscible with water. Methanol and/or ethanol may be included in the solution in an amount of up to 90 volume percent (vol %), based on the total volume of the solution, to control the starting solubility of insulin. For example, methanol and/or ethanol may be included in the acidic solution in an amount preferably of approximately 90 vol % (based on the total volume of the acidic solution), but any amount greater than 0 to up to 90 vol % is contemplated and may be used.

The acidic solution may be placed on top of a stirring plate. Steady, continuous, or substantially continuous stirring at around 40 to 200 rotations per minute (rpm) may be utilized throughout until the solution becomes completely or substantially completely clear. Utilizing a rate of agitation and/or a stirring speed that is too high may cause turbulence and non-uniform mixing, while utilizing a rate of agitation or a stirring speed that is too low may result in insulin particles having an undesirable particle size (e.g., a particle size over or greater than 5 μm). The solution turns clear or substantially clear when insulin is dissociated from solid phase to liquid phase (e.g., when the insulin is dissolved to form the dissolved insulin solution). The dissolution of the insulin may be performed in an acidic environment.

In the second action, the stirring speed may be slowed down to about 30 to 100 rpm, for example, 50 to 75 rpm, or 50 to 60 rpm. The dissolved insulin solution is titrated or slowly titrated with a buffer solution and precipitation of the insulin gradually appears as the dissolved insulin solution changes from a clear or substantially clear solution to a milky whitish suspension including micronized insulin particles.

The insulin and/or insulin analogue may be micronized at a pH of 3 to 9, for example, a pH of 4.5 to 7.5. The buffer solution may be prepared to have a pH of 3 to 10. Consequently, the suspension formed by titrating the dissolved insulin solution may have a pH of 3 to 9.

In the third action, a stabilizing agent having a neutral pH and that is miscible with water is utilized. Examples of the stabilizing agent include an alcohol and/or a ketone. For example, the alcohol may include methanol, ethanol, isopropyl alcohol, or a mixture thereof, but the alcohol is not limited thereto. The ketone may include acetone, but the ketone is not limited thereto. The stabilizing agent stabilizes the micronized insulin particles.

A purification and/or drying process may be performed after the separation of the micronized insulin particles. Any suitable purification and/or drying process available in the art may be utilized, and should be apparent to those of ordinary skill in the art.

FIG. 1 is a process flow chart illustrating an embodiment of a method for micronizing insulin and/or insulin analogues at room temperature. In FIG. 1, an embodiment of a process 100 for micronizing insulin includes dissolving insulin raw material 102, precipitating insulin to form and stabilize a suspension 104, and separating insulin 106.

Embodiments of the present disclosure will now be described with reference to examples for purposes of illustration. The present disclosure, however, is not limited to the examples described herein.

Example 1. Preparation of Inhalable Insulin Particles in a 90 Vol % Methanol Solution 70 mg of biosynthetic human insulin (recombinant insulin available from Sigma-Aldrich) raw material powder was dissolved in 7.7 ml of an acidic solution having a pH of about 1.9 and including 90 vol % of methanol (the other 10 vol % including water and HCl), based on the total volume of the acidic solution, in a 40 ml vial. The vial was placed on top of a stirring plate and the resultant solution was steadily stirred until the solution was completely or substantially clear to form a dissolved insulin solution. Then, the stirring was slowed to a slower mode (e.g., a spinning speed of about 75 rpm), and 1.75 ml of a 0.1 M sodium acetate (NaAc) buffer solution having a pH of 5.64 was added dropwise to slowly titrate the dissolved insulin solution. The clear dissolved insulin solution turned into a milky and yellowish suspension including micronized insulin particles. About 10 ml of ethanol was added to the suspension after the titration was completed or substantially completed. The stirring was continued for another 30 minutes. The micronized insulin particles were separated from a supernatant of the suspension as a solid and the solid was washed with ethanol twice to remove methanol and salt. The solid was vacuum dried at room temperature.

Figure 2:
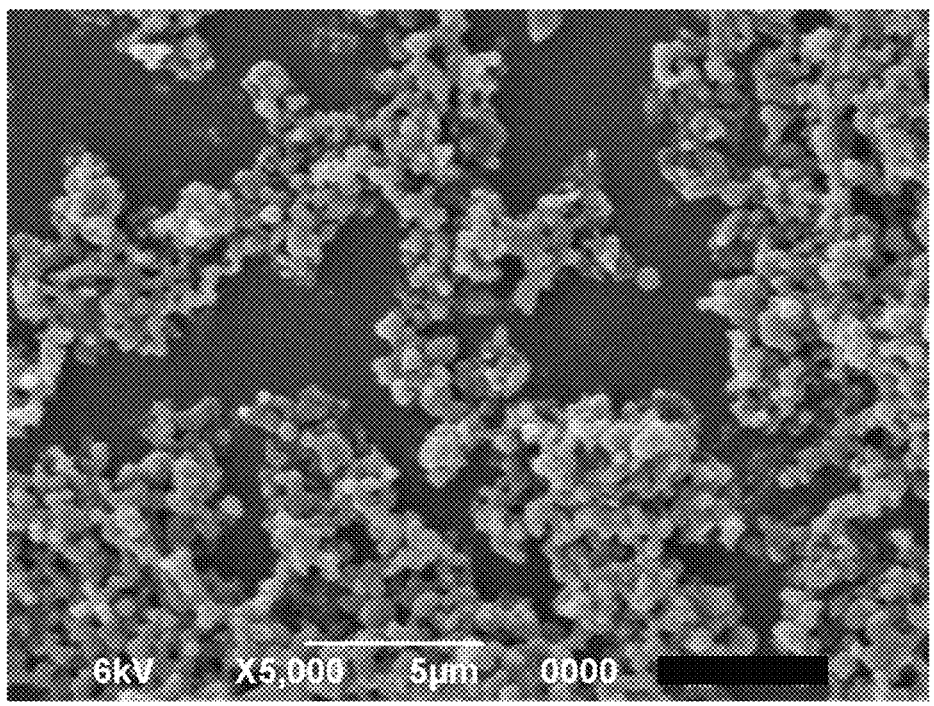
Figure 3:
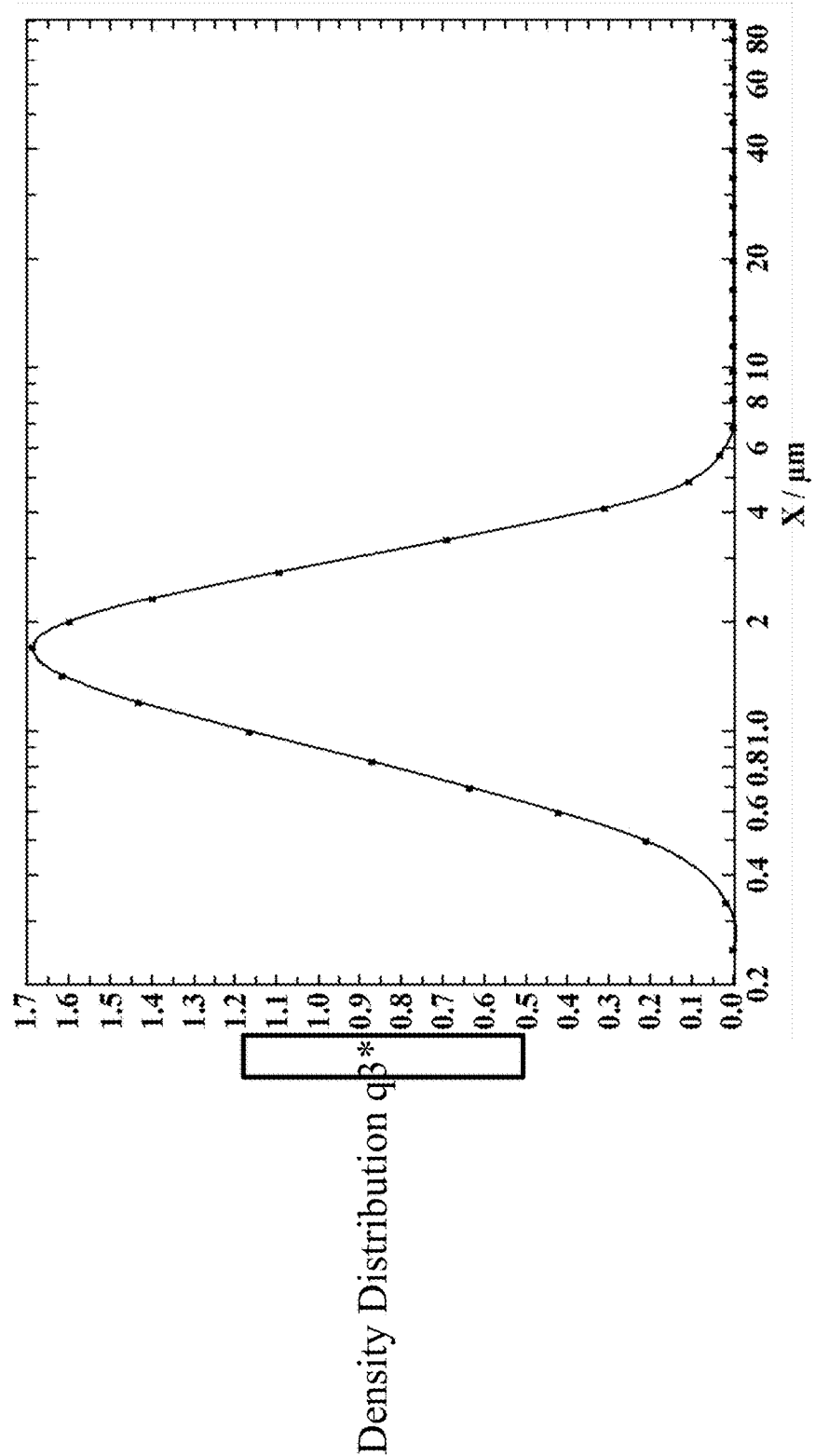
Figure 4:
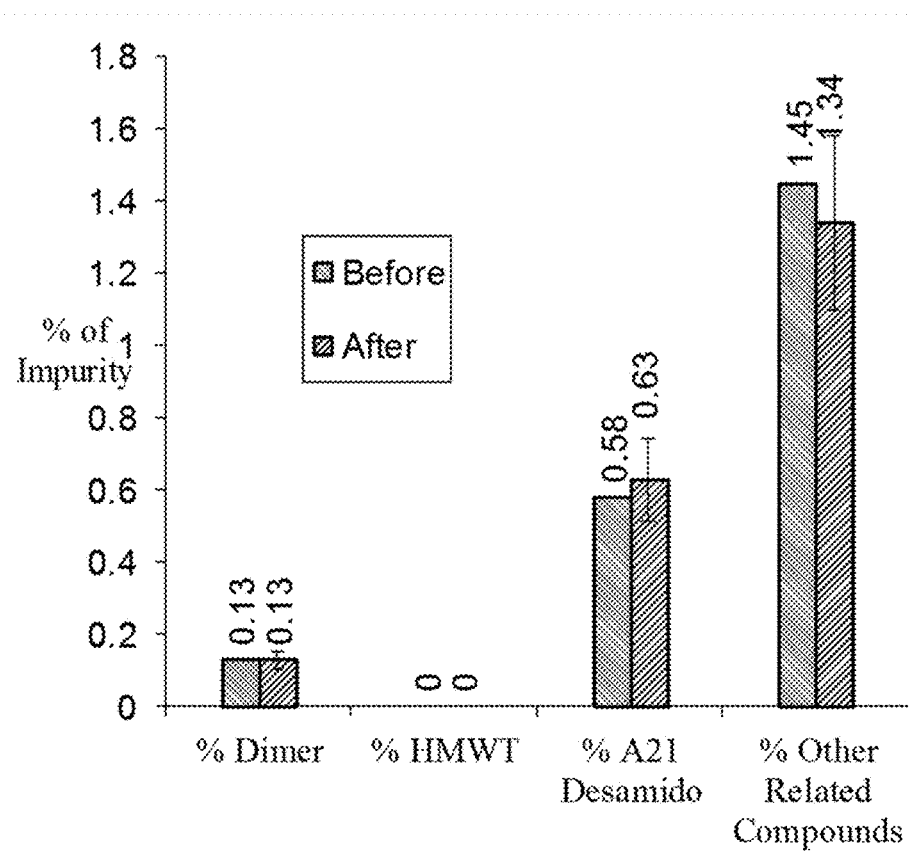
Figure 5:
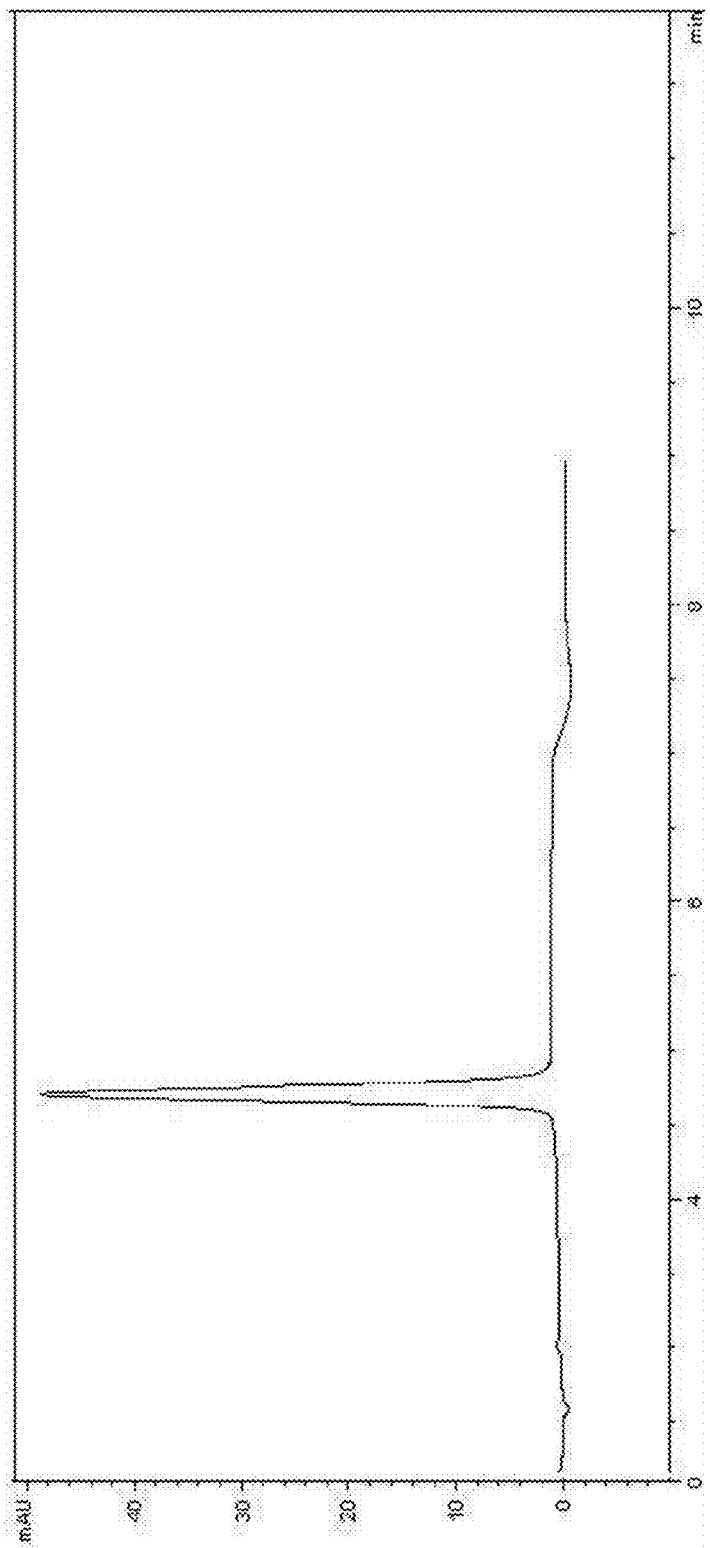
Figure 6:
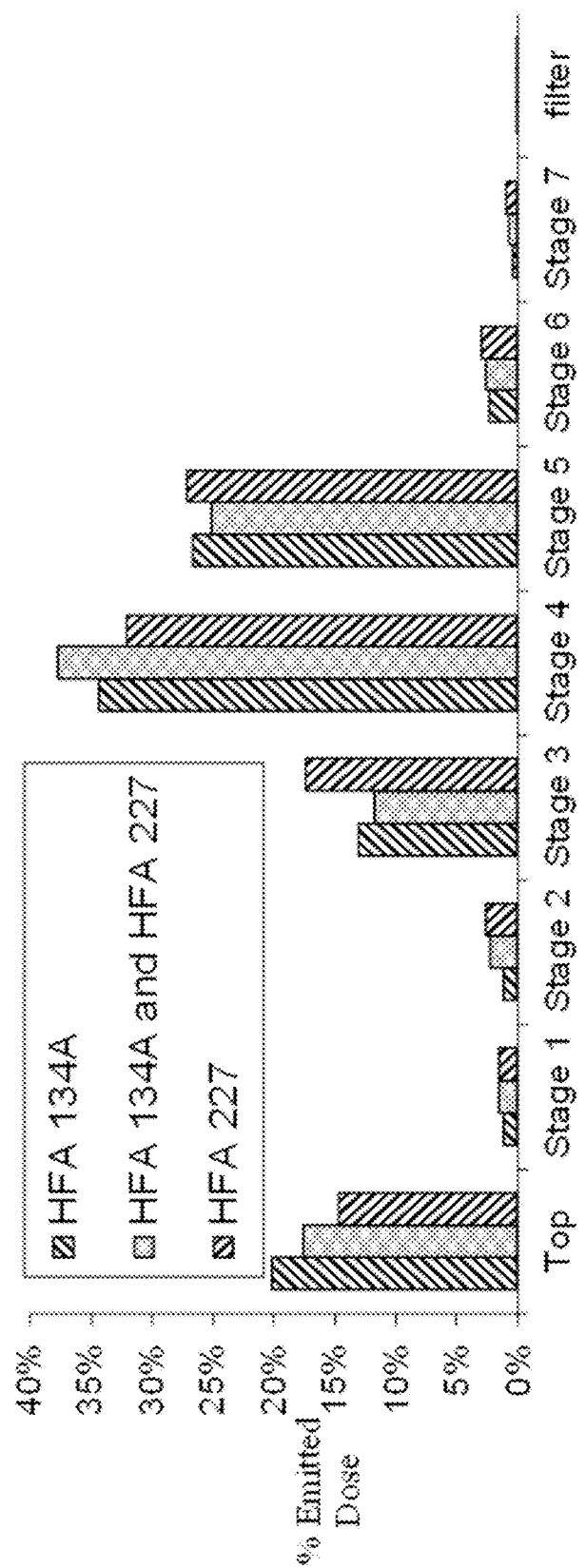

FIG. 2 is a scanning electron microscopy (SEM) image showing the inhalable human insulin API produced via the method described with respect to Example 1. In the present application, all of the SEM images were obtained using a JEOL CarryScope JCM-5700 SEM instrument. FIG. 3 is a graph illustrating the particle size distribution of the inhalable insulin API (micronized insulin) prepared as described with respect to Example 1. It was concluded from FIGS. 2 and 3 that the particle sizes of the inhalable insulin API (micronized insulin) prepared as described with respect to Example 1 are suitable for pulmonary delivery, e.g., have a particle size <5 μm. For example, as can be seen in FIG. 3, the average particle size D50 of the micronized insulin of Example 1 was less than 2 μm. D50 is the maximum particle diameter below which 50 vol % of the sample, based on the total volume of the sample, has a smaller particle diameter and above which 50 vol % of the sample has a larger particle diameter.

Example 2. Batch Process for Preparation of Inhalable Insulin Particles in a 90 Vol % Methanol Solution 1 gram of biosynthetic human insulin API powder (i.e., recombinant insulin from Sigma-Aldrich). was dissolved in 110 ml of an acidic solution having a pH of about 1.9 and including 90 vol % of methanol (the other 10 vol % including water and HCl), based on the total volume of the acidic solution, in a 400 ml container including a centrifugal stirrer or stirring bar. The resultant solution was stirred until the insulin solution was completely or substantially completely clear to form a dissolved insulin solution. Then, the stirring was slowed to a slower mode (e.g., a spinning speed of about 50 rpm), and 25 ml of a 0.1 M NaAc buffer solution (having a pH of 5.64) was added dropwise to titrate the dissolved insulin solution. The clear dissolved insulin solution turned into a milky and yellowish suspension including micronized insulin particles. After the titration was completed or substantially completed, about 135 ml of ethanol was added to the suspension, and the stirring was continued for another 30 minutes.

The micronized insulin particles were separated from the supernatant of the suspension as a solid and the solid was washed with ethanol twice to remove methanol and salt. The solid was vacuum dried at room temperature. The product weight was used to calculate the recovery rate. The particle size was analyzed using a laser diffraction particle size analyzer (i.e., the JEOL CarryScope JCM-5700 SEM instrument).

The above procedures were repeated four (4) times for batches of micronized insulin.

Table 1 shows reproducibility of the recovery rate for the four (4) batches produced as described with respect to Example 2. As can be seen from Table 1, the recovery rate for Example 2 is over 86%.

TABLE 1

| Batch ID | Recovery Rate % |
|---|---|
| 1 | 86.4 |
| 2 | 86.1 |
| 3 | 86.8 |
| 4 | 86.2 |
| Average | 86.4 |
| Standard Deviation | 0.3 |
| Relative Standard Deviation, % | 0.4 |

Table 2 shows the reproducibility of the particle size distribution of the micronized human insulin particles produced in the batches of Example 2. It was concluded from Table 2 that the particles sizes of the micronized insulin prepared as described with respect to Example 2 are suitable for pulmonary delivery, e.g., having a particle size <5 μm. For example, as can be seen in Table 2, for the micronized insulin of Example 2 the average particle size D50 was 1.54 μm, the average particle size D10 was 0.75 μm, and the average particle size D90 was 3.04 μm, which is suitable for pulmonary delivery. D50 is the maximum particle diameter below which 50 vol % of the sample, based on the total volume of the sample, has a smaller particle diameter than the D50 particle diameter and above which 50 vol % of the sample has a larger particle diameter than the D50 particle diameter. D10 is the particle diameter at which 10 vol % of the particles, based on the total volume of the particles, have a smaller particle diameter than the D10 particle diameter. D90 is the particle diameter at which 90 vol % of the particles, based on the total volume of the particles, have a smaller particle diameter than the D90 particle diameter.

TABLE 2

| | Particle Size Distribution (μm) | | | |
|---|---|---|---|---|
| Batch ID | D10 | D50 | D90 | Volume Mean Diameter |
| 1 | 0.72 | 1.46 | 2.9 | 1.68 |
| 2 | 0.77 | 1.58 | 3.0 | 1.77 |
| 3 | 0.75 | 1.52 | 2.95 | 1.74 |
| 4 | 0.76 | 1.59 | 3.31 | 1.96 |
| Average | 0.75 | 1.54 | 3.04 | 1.79 |
| Standard Deviation | 0.02 | 0.06 | 0.18 | 0.12 |
| Relative Standard Deviation | 2.9% | 3.9% | 6.1% | 6.8% |

The chemical stability of the insulin before and after processing was tested by high performance liquid chromatography (HPLC) according to Chapter <621> of United States Pharmacopeia (USP) and USP methods used for impurity test for the human insulin monograph. FIG. 4 is a chart showing an impurity profile of insulin before and after the micronizing process according to Example 2. As can be seen in FIG. 4, there is not a statistically significant change in the quantity of impurities, such as insulin dimers, high molecular weight proteins, A-21 desamido insulin or related compounds in the insulin during the micronizing process.

FIG. 5 is a high-performance liquid chromatography (HPLC) chromatograph of dissolved insulin particles prepared as described in Example 2. The HPLC chromatograph of FIG. 5 shows that the retention time for micronized insulin does not exhibit a statistically significant change with respect to that of the original insulin raw material. The evidence from the analysis of the micronized insulin particles indicates that the chemical integrity of the insulin is maintained or substantially maintained during the micronization process.

The particle size distribution of the micronized insulin particles was evaluated using a laser diffraction CUVETTE CUV-50ML/US instrument from Sympatec Gmbh. The micronized insulin particles were tested in ethanol media (an ethanol solution). The data obtained shows that over 99 vol % of the particles, based on the total volume of the particles, have a particle size smaller than 5 μm and the average of the volume mean diameter for all four (4) batches is 1.79 μm, as shown in Table 2. Thus, the micronized insulin particles may include 99 vol % or more (e.g., 99 to 100 vol %) of particles having a particle size of less than 5 μm, based on the total volume of the micronized insulin particles. In some embodiments, the micronized insulin particles may include up to 99 vol % of particles having a particle size of less than 5 μm, based on the total volume of the micronized insulin particles FIG. 6 is a chart showing Andersen Cascade Impactor studies of the human insulin (API produced as described with respect to Example 2) delivered from three metered dose inhalers utilizing a propellant including 1,1,1,2-tetrafluoroethane (HFA 134A), 1,1,1,2,3,3,3,-heptafluoropropane (HFA 227), or a mixture of HFA 134A and HFA 227, respectively. The metered dose inhalers were prepared as described below with respect to Example 11. It was concluded from the data shown in FIG. 6 that the three different propellants (HFA 134A, HFA 227, and the mixture of HFA 134A and HFA 227) provided comparable results when utilized with the micronized human insulin produced as described with respect to Example 2.

Figure 7:
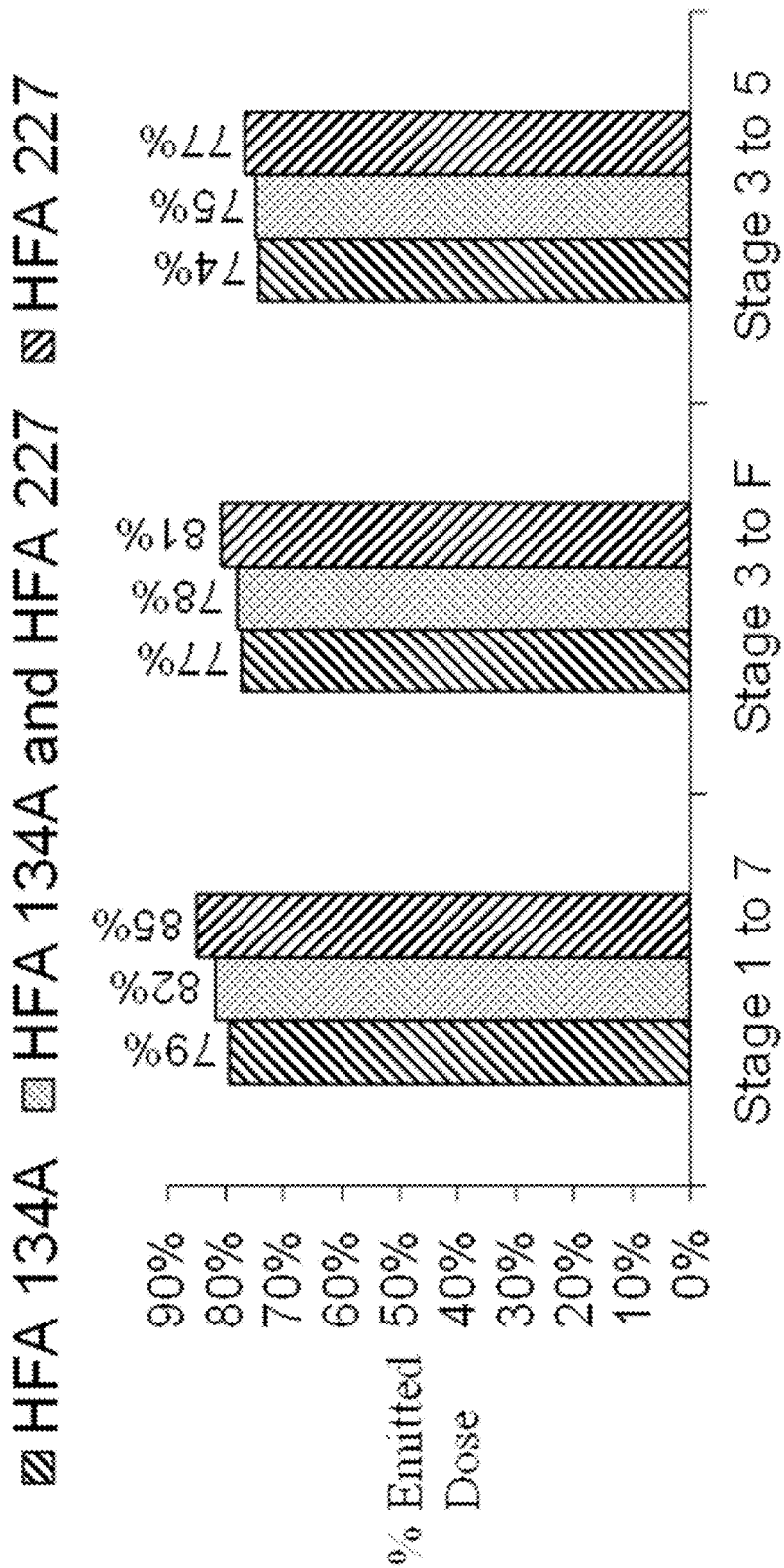

FIG. 7 is a chart further showing the Andersen Cascade Impactor analytical results at three different stage classifications for the human insulin (API produced as described with respect to Example 2) delivered from metered dose inhalers utilizing the three different propellants (HFA 134a, HFA 227, or a mixture of HFA 134A and HFA 227, respectively). The metered dose inhalers were prepared as described below with respect to Example 11. It was concluded from the data shown in FIG. 7 that the three different propellants provided comparable results when utilized with the micronized human insulin produced as described with respect to Example 2.

Example 3. Method of Preparation of Inhalable Insulin Particles in a 100 Vol % Water Solution Inhalable human insulin particles were prepared as described with respect to Example 1, except that a roughly 100 vol % purified water solution having a pH of 2.0 (a solution including purified water and an acid in amount sufficient to provide a pH of 2.0) was used to replace the acidic solution including 90 vol % of methanol of Example 1. The particle size distribution of the resultant inhalable human insulin particles was analyzed as described with respect to Example 2. The results of the particle size distribution analysis showed that the inhalable human insulin particles had a volume mean diameter of 2.01 µm. As noted above, the inhalable human insulin particles prepared as described with respect to Example 1 had a particle size D50 of less than 2 µm, and the average of the volume mean diameter of all 4 batches of the inhalable human insulin particles prepared as described with respect to Example 2 (which were also prepared using an acidic solution including 90 vol % methanol) was 1.79 µm. Thus, it can be seen that the composition of the solvent (e.g. methanol vs. water) can change the size of the micronized human insulin that is produced.

Example 4. Methods of Preparation of Inhalable Human Insulin Particles in Low Methanol Concentration Solution Inhalable human insulin particles were prepared as described with respect to Example 1, except that an acidic solution including 50 vol % methanol at a pH of about 2.0 (the other 50 vol % including water and HCl) or an acidic solution including 10 vol % methanol (the other 90 vol % including water and HCl), based on the total volume of the acidic solution, was used to replace the acidic solution including 90 vol % methanol utilized to dissolve the human insulin raw material of Example 1.

Table 4 shows particle size distribution data of human insulin particles micronized as described with respect to Examples 1, 3 and 4.

TABLE 4

| ID# | Solvent | Particle Size Distribution (µm) | | | Volume Mean Diameter |
|---|---|---|---|---|---|
| | | D10 | D50 | D90 | |
| Example 3 | 100 vol % water | 0.65 | 1.63 | 3.92 | 2.01 |
| Example 4 | 10 vol % MeOH | 0.65 | 1.66 | 3.77 | 2 |

TABLE 4-continued

| ID# | Solvent | Particle Size Distribution (µm) | | | Volume Mean Diameter |
|---|---|---|---|---|---|
| | | D10 | D50 | D90 | |
| Example 4 | 50 vol % MeOH | 0.33 | 0.74 | 1.52 | 0.87 |
| Example 1 | 90 vol % MeOH | 0.72 | 1.51 | 2.94 | 1.71 |

It was therefore concluded that the starting solvent (e.g., methanol solution vs. water) and solvent concentration (e.g., methanol concentration of 10 vol %, 50 vol % or 90 vol %, based on the total volume of the acidic solution) utilized to dissolve human insulin (raw material) may affect the particle size of the micronized human insulin particles.

Example 5. Methods of Preparation of Inhalable Human Insulin Particles in a 10 Vol % Ethanol Solution Inhalable human insulin particles were prepared as described with respect to Example 1, except that an acidic solution including 10 vol % ethanol (the other 90 vol % including water and HCl) having a pH of 2 based on the total volume of the acidic solution, was used to replace the acidic solution including 90 vol % methanol utilized to dissolve the insulin of Example 1. The particle size distribution of the resultant inhalable human insulin particles was analyzed as described with respect to Example 2. The results of the particle size distribution analysis showed that the inhalable human insulin particles had a volume mean diameter of 1.36 μm.

Example 6. Method for Micronizing Human Insulin to Inhalable Particles Utilizing a 90 Vol % Methanol Solution at a Different pH Inhalable human insulin particles were prepared as described with respect to Example 1, except that instead of utilizing a buffer solution having a pH of 5.64 a series of buffer solutions including NaOH having a pH of 3 to 9 were utilized. The particle size distributions of the resultant inhalable human insulin particles were analyzed as described with respect to Example 2. NaOH was used to adjust the solution pH as well. The results of the particle size distribution analyses and the pH of the corresponding buffer solution after titration are shown in Table 5. It was concluded from the data shown in Table 5 that utilizing a buffer solution having a pH of 3 to 9 is suitable for embodiments of the micronization process.

TABLE 5

| | | Particle Size Distribution (μm) | | | |
|---|---|---|---|---|---|
| # | pH | D10 | D50 | D90 | Volume Mean Diameter |
| 1 | 3.1 | 0.5 | 1.16 | 2.32 | 1.31 |
| 2 | 3.7 | 0.58 | 1.35 | 2.91 | 1.59 |
| 3 | 4.9 | 0.66 | 1.43 | 2.9 | 1.65 |
| 4 | 5.3 | 0.63 | 1.29 | 2.4 | 1.42 |
| 5 | 6.0 | 0.7 | 1.44 | 2.27 | 1.63 |
| 6 | 6.2 | 0.72 | 1.51 | 2.94 | 1.71 |
| 7 | 7.0 | 0.6 | 1.22 | 2.21 | 1.33 |
| 8 | 7.9 | 0.56 | 1.17 | 2.12 | 1.28 |
| 9 | 8.8 | 0.57 | 1.18 | 2.13 | 1.29 |

Example 7. Method of Preparation of Inhalable Human Insulin Particle Utilizing an Isopropyl Alcohol Co-solvent Inhalable human insulin particles were prepared as described with respect to Example 1, except that isopropyl alcohol was used to replace the ethanol of Example 1 that was added to the suspension after the titration was completed or substantially completed. The particle size distribution of the resultant inhalable human insulin particles was analyzed as described with respect to Example 2. The results of the particle size distribution analysis showed that the volume mean diameter of the inhalable human insulin particles was 1.27 µm.

Example 8. Method of Preparation of Inhalable Human Insulin Particle Utilizing an Acetone Co-Solvent Inhalable human insulin particles were prepared as described with respect to Example 1, except that acetone was used to replace the ethanol of Example 1 that was added to the suspension after the titration was completed or substantially completed. The particle size distribution of the resultant inhalable human insulin particles was analyzed as described with respect to Example 2. The results of the particle size distribution analysis showed that the volume mean diameter of the inhalable human insulin particles was 1.32 µm.

Figure 8:
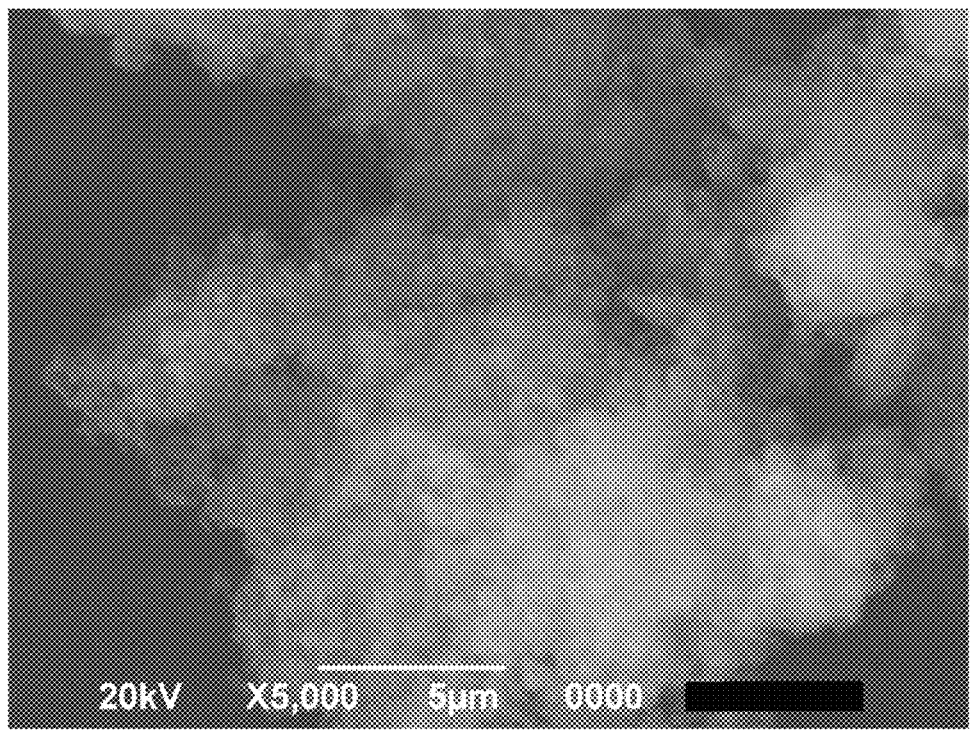
Figure 9:
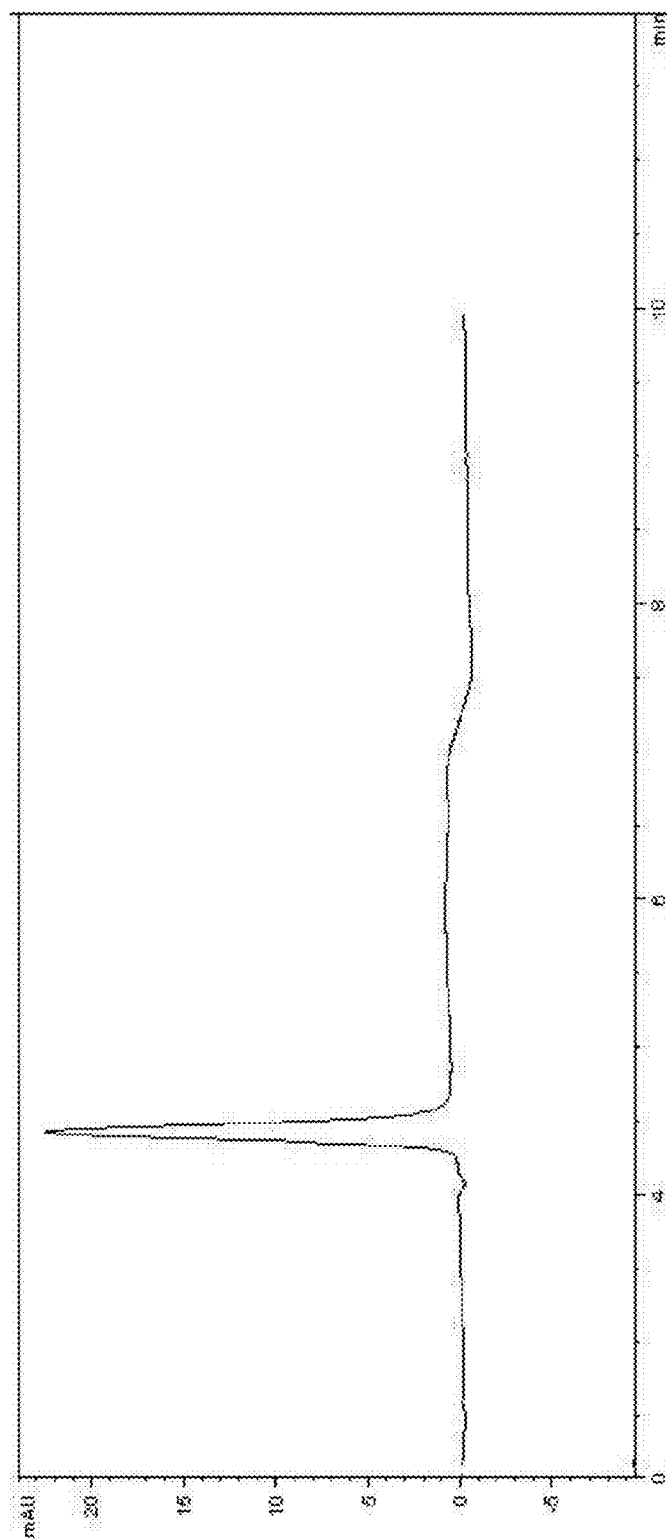
Figure 10:
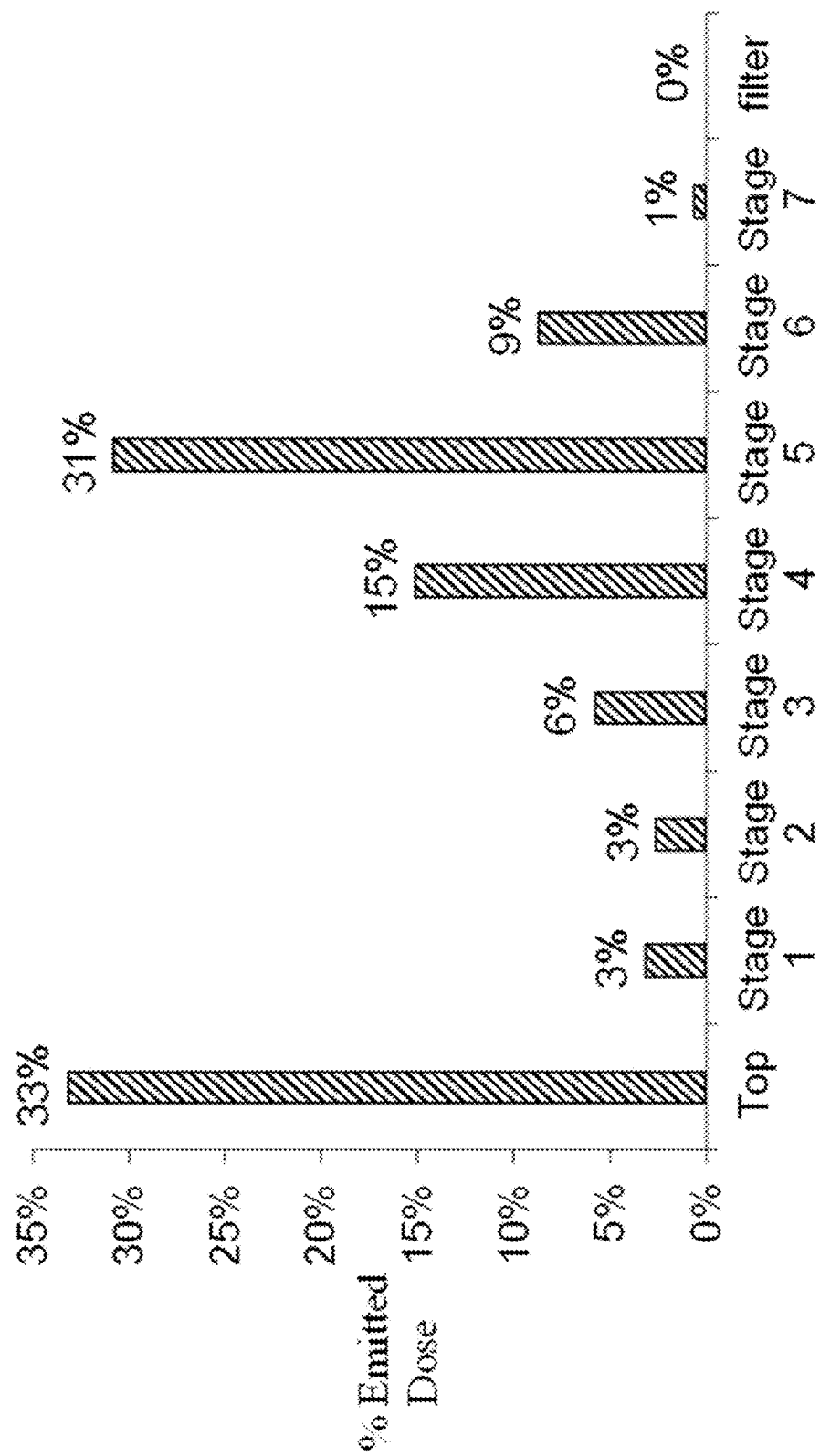
Figure 11:
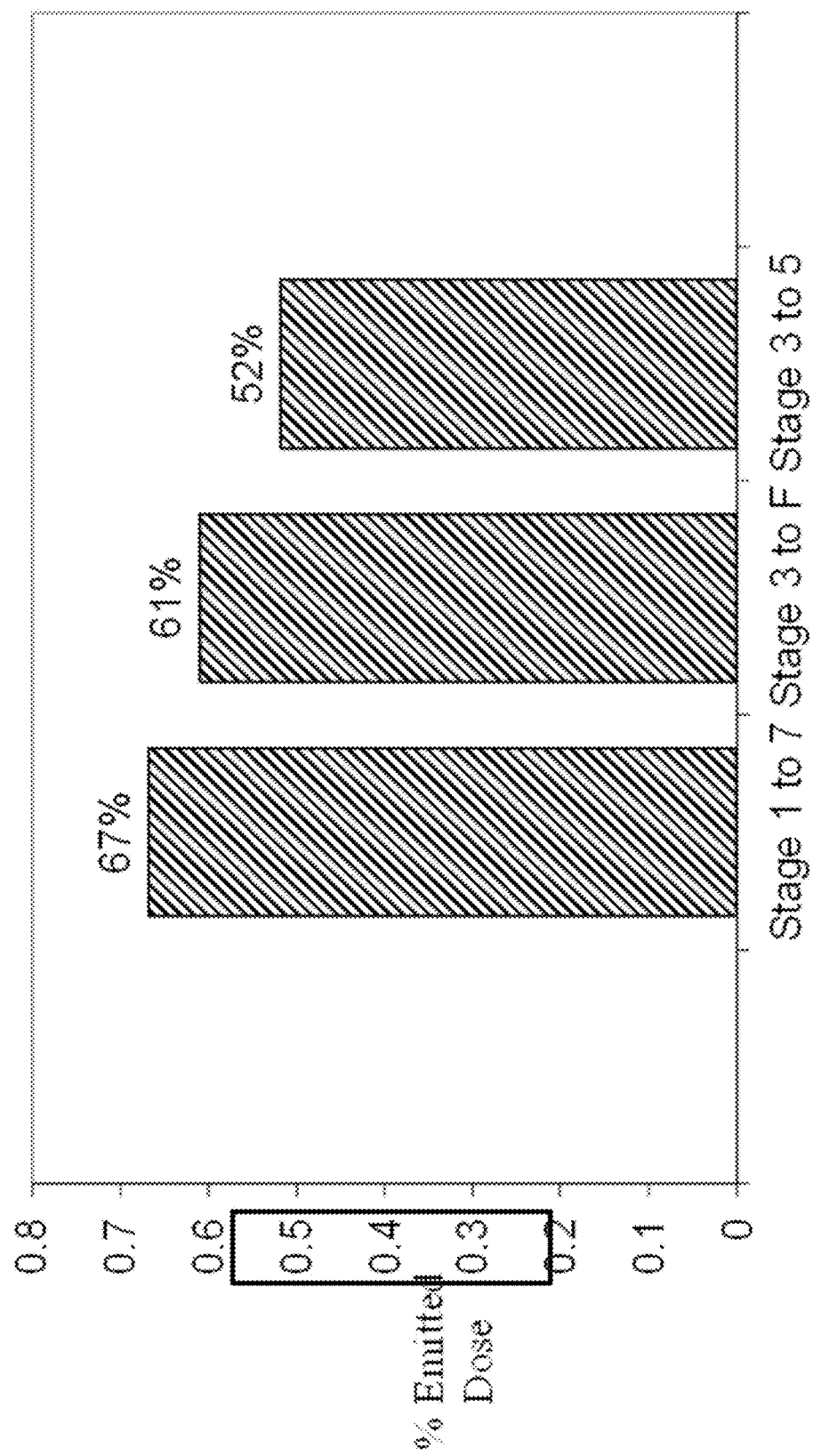

Example 9. Method for Micronizing Insulin Glargine Analogue to Inhalable Particles Insulin glargine is a long acting human insulin analogue. The insulin glargine used here was obtained by ultrafiltration of commercially available insulin glargine (LANTUS®). The insulin glargine was washed and lyophilized before use. 70 mg of the washed and lyophilized insulin glargine was dissolved in 7.7 ml of an acidic solution having a pH of about 2.2 and including 90 vol % methanol (the other 10 vol % including water and HCl), based on the total volume of the acidic solution, to form a dissolved insulin solution including an insulin glargine. 1.75 ml of a phosphate buffer solution having a pH of 6.9 was added dropwise to titrate the dissolved insulin glargine solution after the insulin glargine was completely or substantially completely dissolved. 10 ml of ethanol was added to the solution. The foregoing dissolving, titrating, and addition of ethanol were performed under steady (substantially continuous) stirring. The clear dissolved insulin glargine solution becomes a milky suspension including micronized insulin glargine particles (micronized insulin glargine particles). The micronized insulin glargine particles were separated, washed and dried. The particle size distribution of the micronized insulin glargine particles was analyzed using the laser diffraction test described with respect to Example 2. The particle distribution analysis showed that the volume mean diameter of the micronized insulin glargine particles was 2.27 µm. FIG. 8 is a Scanning Electron Microscopy (SEM) image of the micronized insulin glargine particles. FIG. 9 is an HPLC chromatograph of the dissolved micronized insulin glargine particles. Retention time of the HPLC results shown in FIG. 9 indicates that the chemical properties of the insulin glargine did not change (or did not substantially change) during the micronization process. FIGS. 10 and 11 are charts showing the results of an Andersen Cascade Impactor study of the insulin glargine particles delivered from metered dose inhalers utilizing HFA 134A as a propellant. The metered dose inhalers were prepared as described below with respect to Example 11. The study results shown in FIGS. 10 and 11 demonstrated a consistent or substantially consistent pattern.

Figure 12:
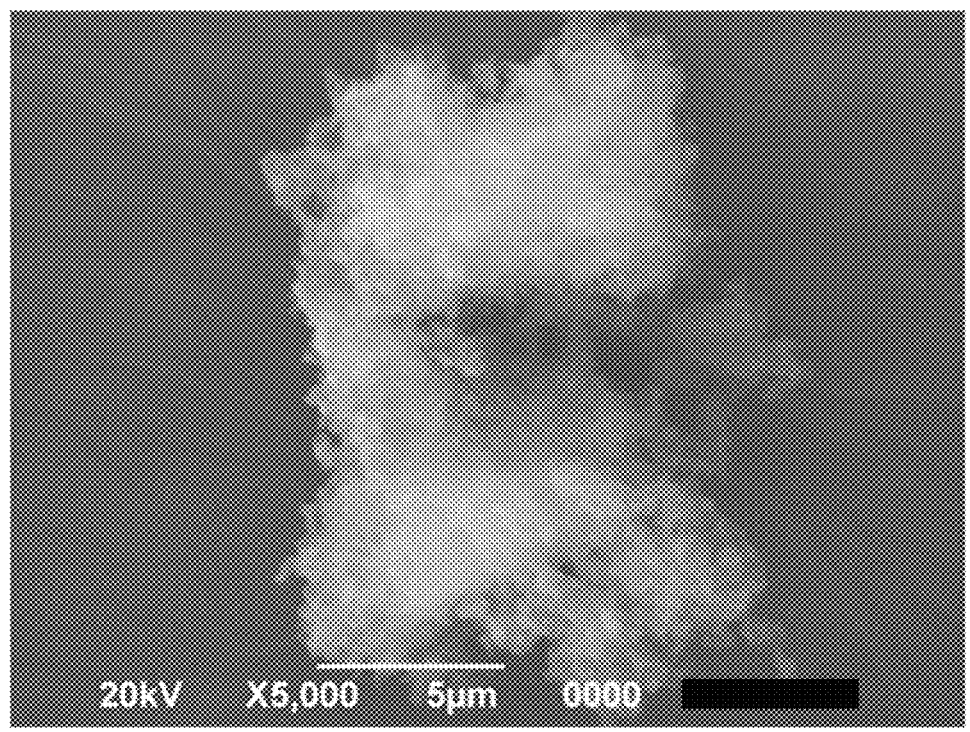
Figure 13:
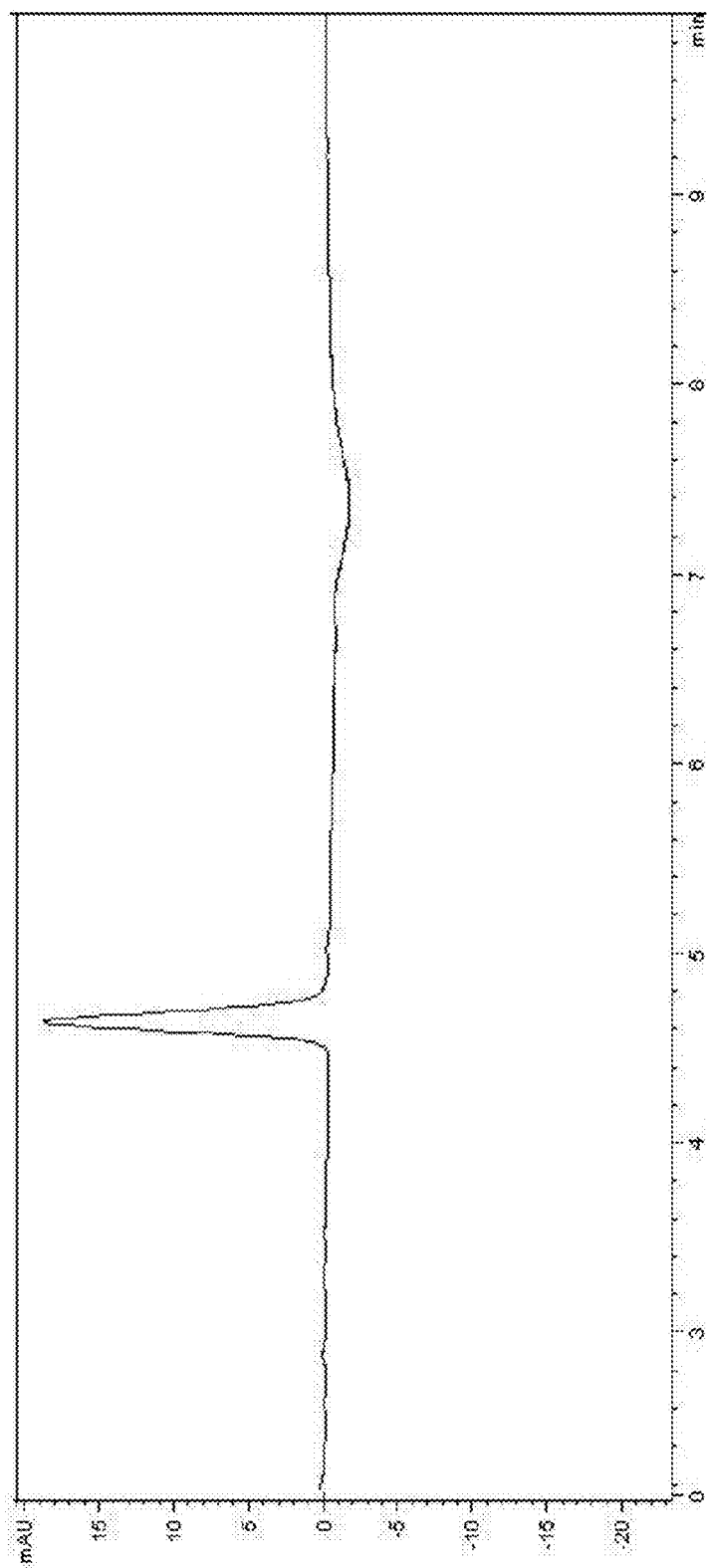

Example 10. Method for Micronizing Insulin Aspart Analogue to Inhalable Particles Insulin Aspart is a fast-acting insulin analogue. Insulin Aspart used here was obtained by ultrafiltration of Novo-Log® (obtained from Novo Nordisk, Bagsverd, Denmark). The ultrafiltered insulin aspart was washed and lyophilized before use. 70 mg of washed and lyophilized insulin aspart was dissolved in 7.7 ml of an acidic water solution having a pH of about 2 and including HCl to form a dissolved insulin solution including insulin aspart. 4.2 ml of an acetate buffer solution having a pH of 5.64 was added dropwise to titrate the dissolved insulin aspart solution after the insulin aspart was completely or substantially completely dissolved. 78 ml of ethanol was added to the solution to obtain a suspension. The foregoing dissolving, titrating, and addition of ethanol were performed under steady (substantially continuous) stirring. The clear dissolved insulin aspart solution became a milky suspension including micronized insulin aspart particles (micronized insulin aspart particles). The micronized insulin aspart particles were separated, washed and dried. The particle size distribution of the micronized insulin aspart particles was analyzed using the laser diffraction test described with respect to Example 2. The particle distribution analysis showed that the volume mean diameter of the micronized insulin aspart particles was 2.72 µm. FIG. 12 is a Scanning Electron Microscopy (SEM) image of the micronized insulin aspart particles. FIG. 13 is an HPLC chromatograph of the dissolved micronized insulin aspart particles. Retention time of the HPLC results shown in FIG. 13 indicates that the chemical properties of the insulin aspart did not change (or did not substantially change) during the micronization process.

Figure 14:
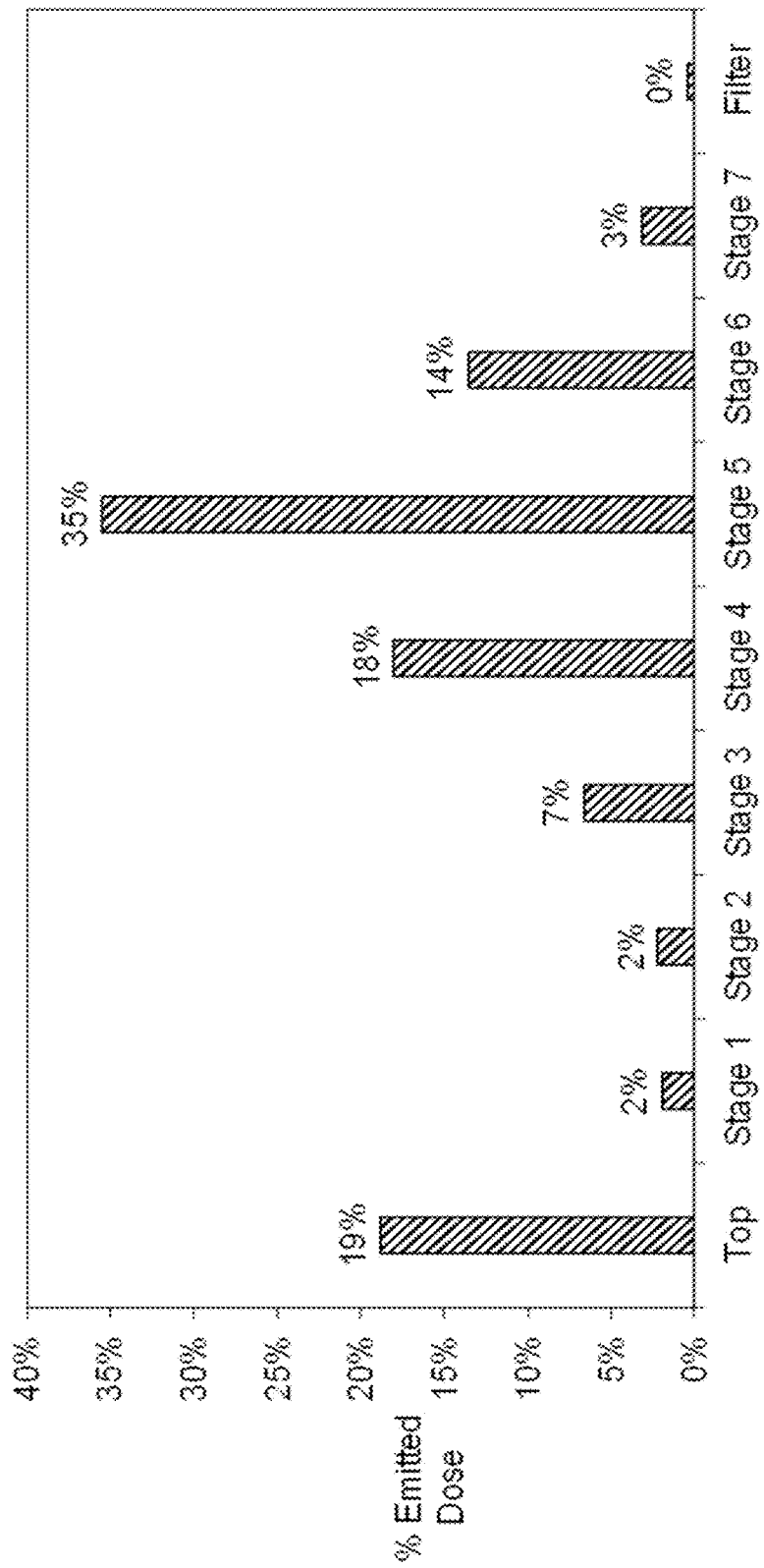
Figure 15:
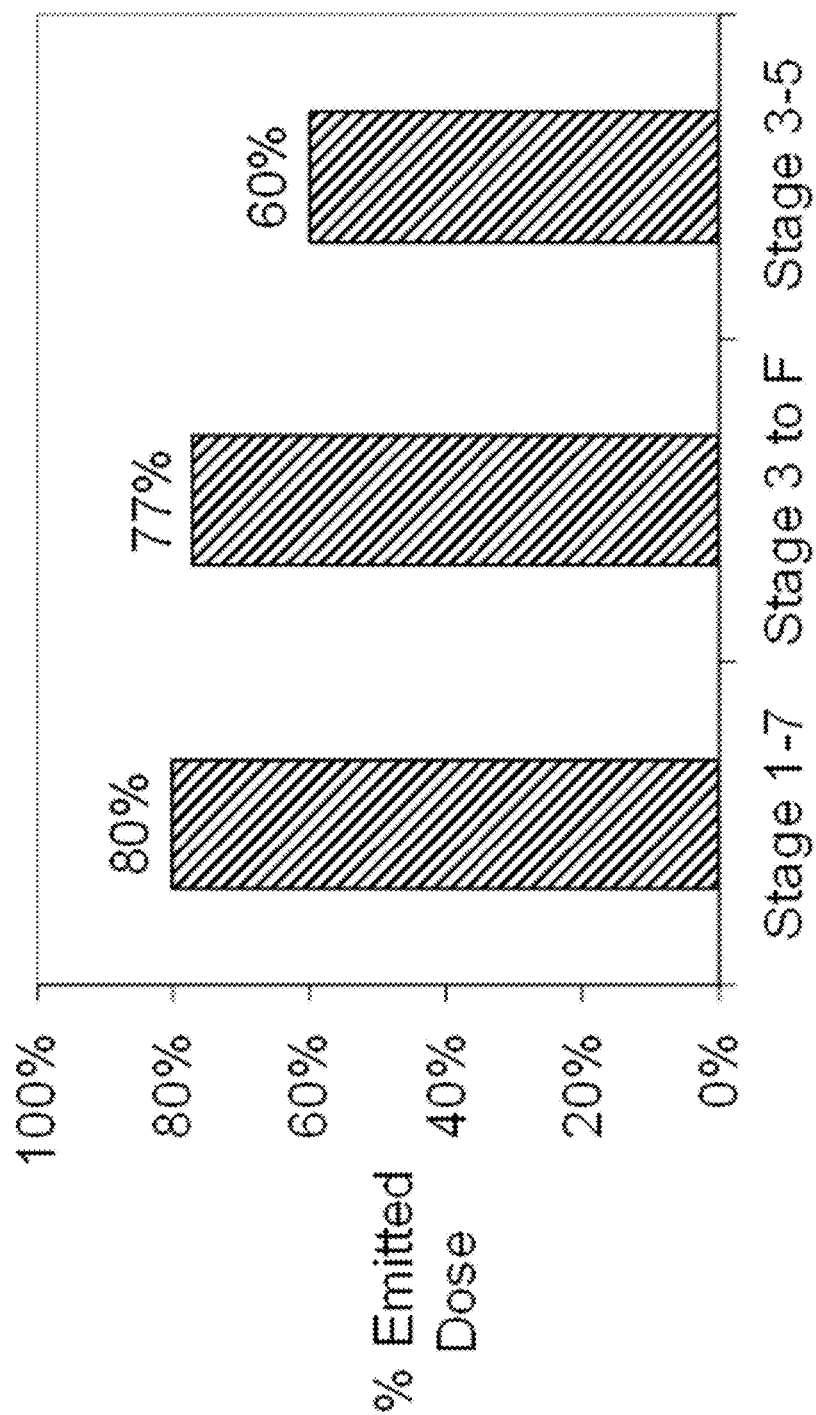

FIGS. 14 and 15 are charts showing the results of an Andersen Cascade Impactor study of the insulin aspart particles delivered from metered dose inhalers utilizing HFA 134A as a propellant. The metered dose inhalers were prepared as described below with respect to Example 11. The study results shown in FIGS. 14 and 15 demonstrated a consistent or substantially consistent pattern.

Example 11. Preparation of Metered Dose Inhalers for In Vitro Andersen Cascade Impactor Tests Metered dose inhalers (MDIs) were prepared according to the following process. A suitable or appropriate amount of micronized human insulin API (e.g., micronized human insulin particles or micronized human insulin analogue particles) and ethanol were filled into an inhaler canister. The contents of the canister were then mixed by applying ultrasonic energy using a VWR Aquasonic for 5 mins to achieve a uniform or substantially uniform suspension. Different propellants such as HFA 134A, HFA 227 or a mixture thereof were added, and the canister was sealed utilizing a suitable valve by clamping.

Micronized human insulin (e.g., micronized human insulin particles or micronized insulin analogue particles) was filled into the metered dose inhaler (MDI) as the active ingredient. The concentration of human insulin or insulin analogue in the inhaler was 3 mg/g. The Andersen Cascade Impactor data shown in FIG. 7, FIG. 11, and FIG. 15 correspond well with the particle size distribution results observed utilizing a laser diffraction particle size analyzer. In the Andersen Cascade Impactor data provided herein, emitted dose refers to the percentage of the human insulin or insulin analogue that was deposited on the Andersen Cascade Impactor.

The shape and roughness (or smoothness) of the surface of the human insulin particles micronized by embodiments of the process disclosed herein is quite suitable or favorable (e.g., suitable or favorable for pulmonary delivery). Micronization by jet milling is a common way to grind particles from a millimeter size range to a smaller micrometer size range. The jet milling process involves frequent collisions among the particles as well as collisions with a wall of a milling chamber caused by a high speed gas stream. The micronized particles produced by jet milling are extracted from the milling chamber by a circular motion of a gas stream and centrifugal forces. These mechanical forces may damage the surface and the shape of the micronized particles, for example, as described below with respect to Comparative Example 1, which may not be favorable or suitable for pulmonary delivery.

Comparative Example 1. Preparation of Human Insulin Particles Via Jet Milling

Figure 16:
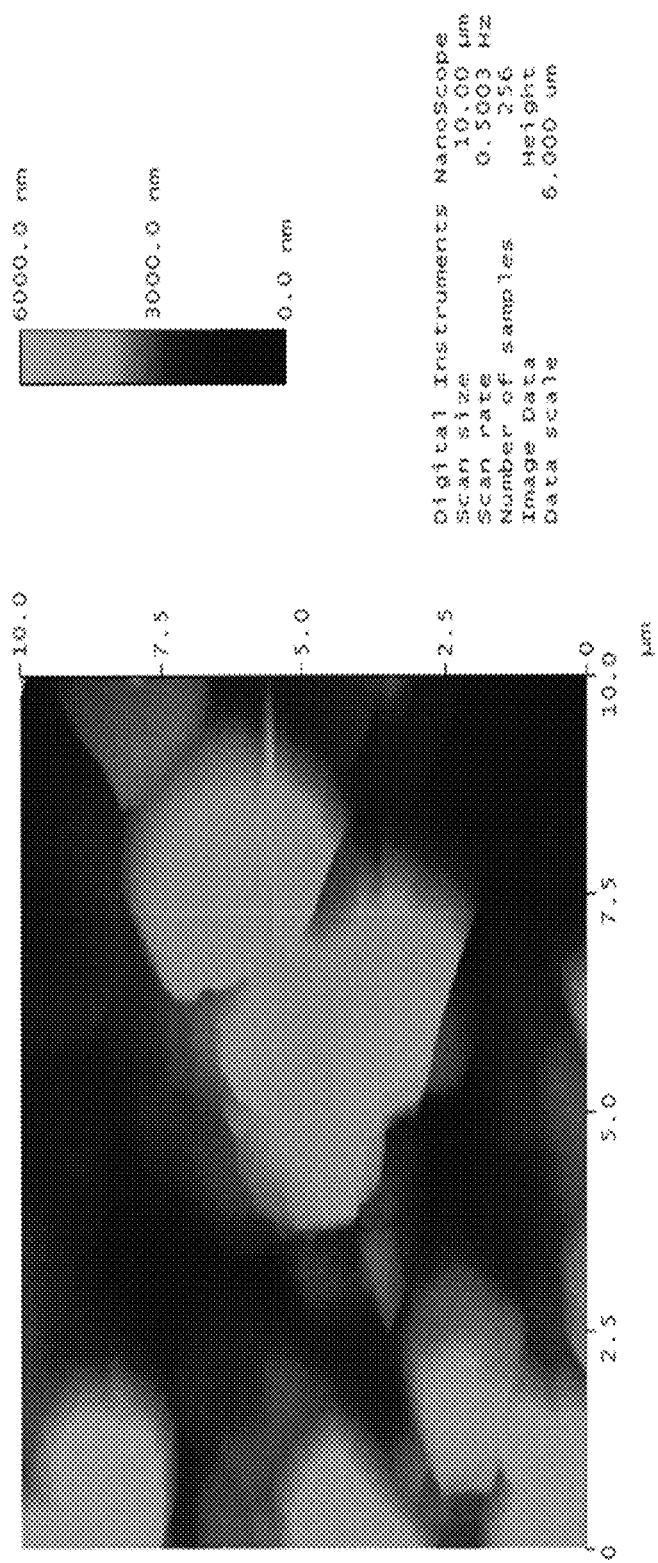

Human Insulin particles were prepared by jet milling utilizing a grinding $N_2$ pressure of 75 PSI and a feeding rate about 1 g/min. FIG. 16 is an atomic force microscopy (AFM) image of human insulin particles that were micronized using the jet milling method. As can be seen in the image of FIG. 16, the human insulin particles prepared by jet milling have a rough and irregular (or uneven) appearance.

Figure 17:
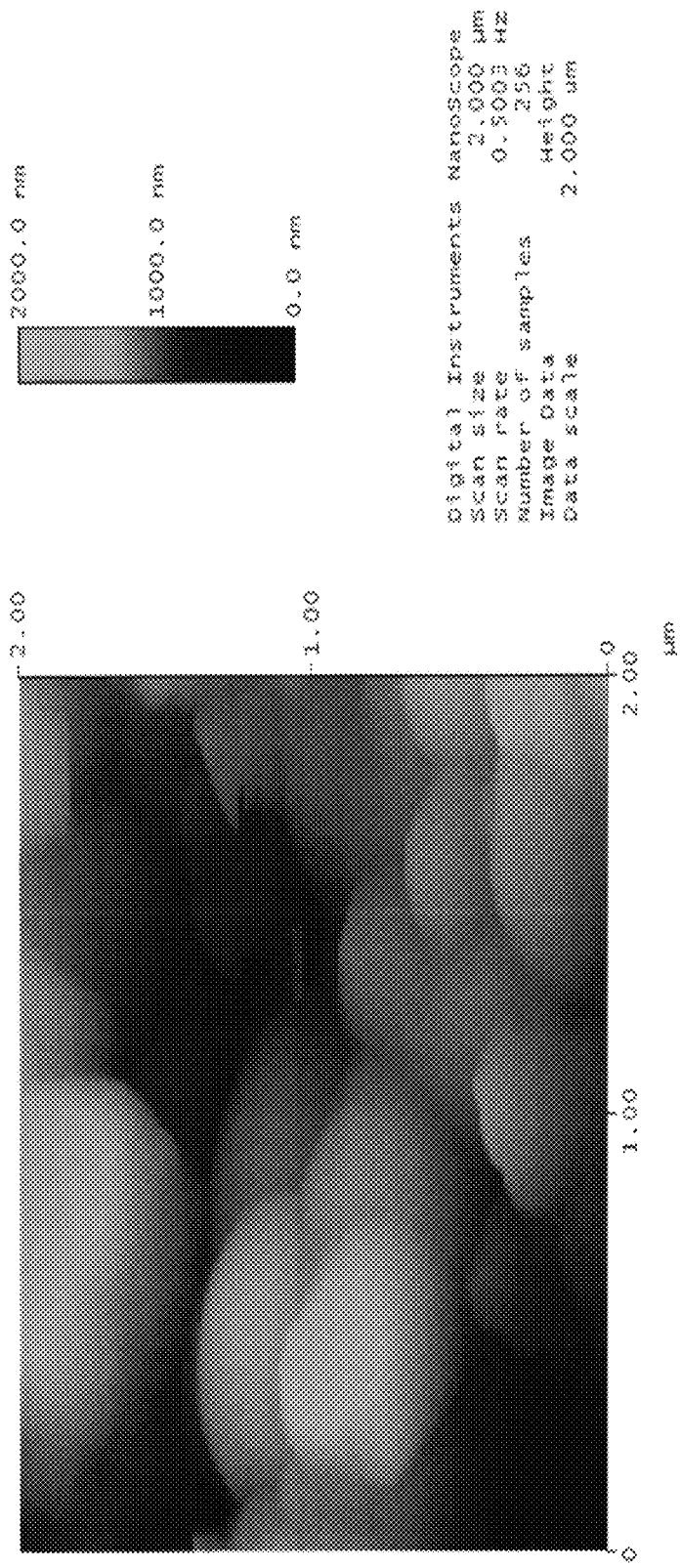

FIG. 17 is an AFM image of inhalable human insulin particles micronized as described with respect to Example 2. Since embodiments of the process disclosed herein are carried out at room temperature and involve no mechanical forces and/or heat (or substantially no mechanical forces and/or heat), the micronized human insulin particles have a shape and surface that are more suitable or more preferred for human pulmonary delivery.

While the present invention has been described in connection with certain embodiments, it is to be understood that the invention is not limited to the disclosed embodiments, but, on the contrary, is intended to cover various modifications and equivalent arrangements included within the spirit and scope of the appended claims, and equivalents thereof. Throughout the text and claims, the terms "about" and "substantially" are used as terms of approximation, not terms of degree, and reflect the inherent variation associated with measurement, significant figures, and interchangeability, all as understood by a person having ordinary skill in the relevant art. Also, it is to be understood that throughout this disclosure and the accompanying claims, even values that are not preceded by the term "about" are also implicitly modified by that term, unless otherwise specified.

What is claimed is:

1. A method of preparing an inhalable insulin suitable for pulmonary delivery, the method comprising:
    dissolving an insulin raw material in an acidic solution to form a dissolved insulin solution;
    titrating the dissolved insulin solution with a buffer solution to form a suspension comprising micronized insulin particles; and
    stabilizing the micronized insulin particles after titrating the dissolved insulin solution,
    wherein the stabilizing of the micronized insulin particles comprises adding a stabilizing agent to the suspension, wherein the stabilizing agent is selected from the group consisting of an alcohol, a ketone, and a mixture thereof,
    wherein the inhalable insulin suitable for pulmonary delivery comprises the micronized insulin particles, the micronized insulin particles are substantially spherical in shape, and the micronized insulin particles comprise up to 99 vol % particles having a particle size of less than 5 µm, based on the total volume of the micronized insulin particles, and
    wherein the micronized insulin particles consist of insulin.

2. The method of claim 1, wherein the acidic solution comprises one selected from the group consisting of water, an organic solvent, and a mixture thereof.

3. The method of claim 2, wherein the acidic solution comprises the organic solvent in an amount of 10 to 90 vol %, based on the total volume of the acidic solution.

4. The method of claim 2, wherein the acidic solution comprises the organic solvent in an amount up to 90 vol %, based on the total volume of the acidic solution.

5. The method of claim 2, wherein the organic solvent comprises an alcohol.

6. The method of claim 5, wherein the alcohol is selected from the group consisting of methanol, ethanol, and a mixture thereof.

7. The method of claim 1, wherein the buffer solution has a pH of 3 to 7.

8. The method of claim 1, wherein the stabilizing agent has a neutral pH and is miscible with water.

9. The method of claim 1, wherein the stabilizing agent is a ketone that stabilizes the micronized insulin particles.

10. The method of claim 1, wherein the micronized insulin particles are micronized at a pH of 3 to 7.

11. The method of claim 1, wherein the micronized insulin particles are micronized at a pH of 4.5 to 6.9.

12. The method of claim 1, wherein the substantially spherical particles have a volume mean diameter of about 1.2 to 2 µm.

13. The method of claim 1, wherein the acidic solution has a pH of 1.0 to 3.0.

14. The method of claim 1, wherein the acidic solution has a pH of 1.8 to 2.2.

15. The method of claim 1, wherein the acidic solution has a pH of about 2 and comprises water and 10 vol % to 90 vol % of an organic solvent selected from the group consisting of methanol, ethanol, and a mixture thereof, based on the total volume of the acidic solution.

16. The method of claim 1, wherein the micronized insulin particles comprise an insulin selected from the group consisting of human insulin, an animal insulin, an insulin analogue, and a mixture thereof.

17. The method of claim 16, wherein the insulin analogue is selected from the group consisting of insulin aspart, insulin glargine, and a mixture thereof.

18. The method of claim 1, wherein one selected from the dissolving, the titrating, the stabilizing, and a combination thereof are performed at room temperature.

19. The method of claim 1, wherein the insulin raw material comprises a crystalline insulin selected from the group consisting of crystalline human insulin, a crystalline animal insulin, a crystalline insulin analogue, and a mixture thereof.

20. The method of claim 19, wherein the crystalline insulin analogue is selected from the group consisting of crystalline insulin aspart, crystalline insulin glargine, and a mixture thereof.

* * * * *